(12) United States Patent
Park et al.

(10) Patent No.: US 8,927,672 B2
(45) Date of Patent: Jan. 6, 2015

(54) BENZINDOCYANINE COMPOUND FOR LABELING SUBSTANCE, INTERMEDIATE THEREOF, AND METHOD FOR PREPARING THE SAME

(75) Inventors: Jin Woo Park, Icheon (KR); Jong Joo Na, Seoul (JP); Doo-Young Chung, Incheon (KR)

(73) Assignee: DKC Corporation, Namdong-Gu, Incheon (KR)

( * ) Notice: Subject to any disclaimer, the term of this patent is extended or adjusted under 35 U.S.C. 154(b) by 91 days.

(21) Appl. No.: 13/695,742

(22) PCT Filed: Mar. 31, 2011

(86) PCT No.: PCT/KR2011/002255
§ 371 (c)(1),
(2), (4) Date: Jan. 8, 2013

(87) PCT Pub. No.: WO2011/139022
PCT Pub. Date: Nov. 10, 2011

(65) Prior Publication Data
US 2013/0102752 A1    Apr. 25, 2013

(30) Foreign Application Priority Data

May 5, 2010  (KR) ........................ 10-2010-0042210

(51) Int. Cl.
C09B 23/06    (2006.01)
G01N 33/533   (2006.01)
C09B 23/08    (2006.01)

(52) U.S. Cl.
CPC ............... *C09B 23/083* (2013.01); *C09B 23/06* (2013.01); *C09B 23/086* (2013.01); *G01N 33/533* (2013.01)
USPC .......................................... 527/201; 548/427

(58) Field of Classification Search
None
See application file for complete search history.

(56) References Cited

U.S. PATENT DOCUMENTS

| 3,282,918 A * | 11/1966 | Hoeksema et al. .......... 536/16.2 |
| 5,268,486 A * | 12/1993 | Waggoner et al. ............ 548/427 |
| 6,043,025 A * | 3/2000 | Minden et al. ..................... 435/4 |
| 6,127,134 A * | 10/2000 | Minden et al. ................. 435/7.2 |
| 2009/0320919 A1 * | 12/2009 | Tsuchiya et al. .............. 136/256 |
| 2011/0128522 A1 | 6/2011 | Usami |

FOREIGN PATENT DOCUMENTS

JP    2009238672 A    10/2009

OTHER PUBLICATIONS

English Translation of the International Preliminary Report on Patentability, IB/Geneva, issued Nov. 6, 2012, incorporating the English Translation of the Written Opinion of the ISA, ISA/KR, mailed Dec. 26, 2011 (6 pages).

* cited by examiner

*Primary Examiner* — James J. Seidleck
*Assistant Examiner* — Peter A Salamon
(74) *Attorney, Agent, or Firm* — Harness, Dickey & Pierce, P.L.C.

(57) ABSTRACT

The present disclosure relates to a novel benzindocyanine compound for labeling biomolecules and a method for preparing the same.

14 Claims, 2 Drawing Sheets

BENZINDOCYANINE COMPOUND FOR LABELING SUBSTANCE, INTERMEDIATE THEREOF, AND METHOD FOR PREPARING THE SAME

CROSS-REFERENCE TO RELATED APPLICATIONS

This application is a National Phase Entry of International Application No. PCT/KR2011/002255, filed on Mar. 31, 2011, which claims priority to Korean Patent Application Serial No. 10-2010-0042210, filed on May 5, 2010, both of which are incorporated by reference herein.

TECHNICAL FIELD

The present disclosure relates to a novel benzindocyanine compound capable of fluorescent labeling of various biomolecules and a method for preparing the same.

BACKGROUND

The functional group of a protein that can react with the functional group of a dye molecule can be inferred from the amino acid of the protein. Specific examples include the amino group ($-CH_2CH_2CH_2CH_2NH_2$) of lysine, the thiol group ($-CH_2SH$) of cysteine, the imidazolamino group

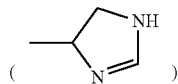

of histidine, the secondary aliphatic hydroxyl group ($-CH_2CH(OH)CH_3$) of threonine, the primary aliphatic hydroxyl group ($-CH_2OH$) of serine, the phenol hydroxyl group

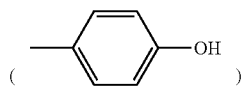

of tyrosine, and so forth. The binding may also occur at the N-terminal amino group ($-COCHRNH_2$) of an amino acid. Also, the functional group of a dye may bind to biomolecules such as sugars, glycoproteins, antibodies, and so forth.

The functional groups of the currently known dyes or other substances used to label biomolecules may be classified according to the functional groups of the biomolecules to which they bind to. They are frequently referred to by their common names.

The most frequently used functional groups for binding to the amino group of a protein molecule are succinimidyl ester and isothiocyanate, and the functional group the most frequently used for binding to the thiol group of a protein molecule is maleimide. For binding to the hydroxyl group of a protein molecule, the following functional groups are used:

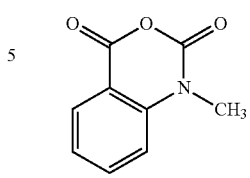

Methylisatoic anhydride

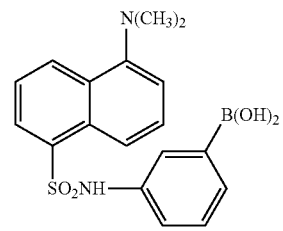

m-dansylaminophenylboronic acid

In addition to the above-described functional groups, many researchers and companies are designing intermediates exhibiting better performance. Although they exhibit fast reaction with most biomolecules as well as superior binding ability, they are usually unstable in aqueous solutions or susceptible to heat and byproducts are often formed after the reaction as the leaving group is detached.

Recently, water-soluble fluorescent dyes are used actively in the bioindustries. For a water-soluble fluorescent dye to be introduced into biomolecules, it needs to experience less photobleaching and quenching in aqueous solutions or under hydrophilic conditions, have a large molar extinction coefficient so as to absorb a large amount of light, fluoresce in the visible or near-infrared region of 500 nm or above distant from the fluorescence range of the biomolecule itself, and be stable under various pH conditions. Due to these requirements, the structures of dyes that can be used for biomolecule labeling are restricted.

Not all dyes fluoresce. Researchers of various fields have developed dyes having chromophores capable of fluorescing. Representative examples of fluorophores known to date include anthranilates, 1-alkylthic isoindoles, pyrrolinones, bimanes, benzoxazoles, benzimidazoles, benzofurazans, naphthalenes, coumarins, stilbenes, carbazoles, phenanthridines, anthracenes, acridines, fluoresceins, eosins, rhodamines, pyrenes, chrysenes, and the like. Derivatives similar to those fluorophores in structure are also studied. These fluorophores are incorporated into various functional groups for binding to biomolecules and are commercially available as various products.

It is to be noted that these fluorescent dyes should exhibit strong fluorescence in media in which most biomolecules are present, that is, in aqueous solutions, in order that the dyes are applicable to the field of biology. The most commonly used fluorescent dyes for such application include xanthan-based fluoresceins and rhodamines and polymethine-based cyanines. For various applications, numerous researchers have introduced pigments and fluorescent dyes for labeling biomolecules into which functional groups capable of binding to protein nucleophiles, i.e. amino, thiol and hydroxyl group, and electrophiles, i.e. aldehyde, ketone and carboxylic acid groups, are incorporated.

Generally, cyanine dyes exhibit excellent optical and pH stability, have narrow absorption and emission wavelength ranges, and fluoresce in the range of 500-800 nm. Since this fluorescence range does not overlap with the autofluorescence range of biomolecules, it is easy to analyze. In addition, the cyanine dyes exhibit high molar extinction coefficients, although there are slight differences depending on solvents and solubility characteristics. The following chemical formulas are the general structures of cyanine dyes known in the literatures and the basic structures of hetero compounds known as derivatives.

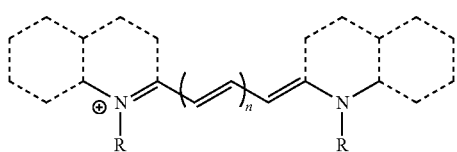

Generic Cyanine Dye

The most commonly used cyanine dyes commercially available are the compounds having indoles as hetero rings and succinimidyl ester groups capable of binding to the amino group of an amino acid as reactive functional groups. For example, GE Healthcare's U.S. Pat. Nos. 5,268,486, 6,043,025 and 6,127,134 and WO96/33406 disclose introduction of various succinimidyl ester groups into cyanine dyes and labeling of biomolecules such as antibodies, peptides, etc. The following chemical formulas are representative structures of cyanine dyes, which are commercially available from GE Healthcare under the trade names Cy3, Cy5 and Cy7.

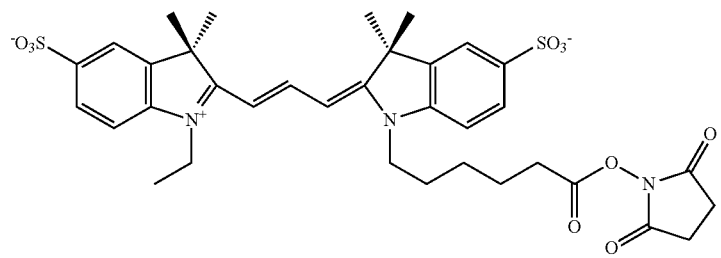

Cy3 (Commercial)

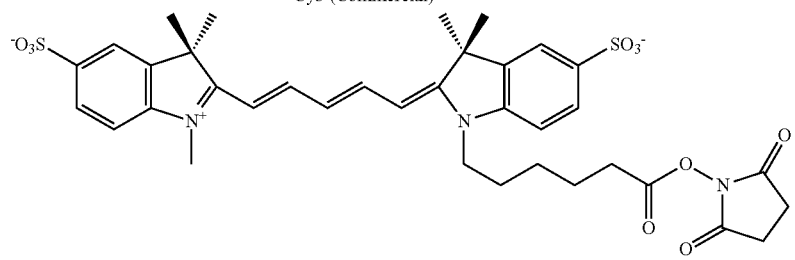

Cy5 (Commercial)

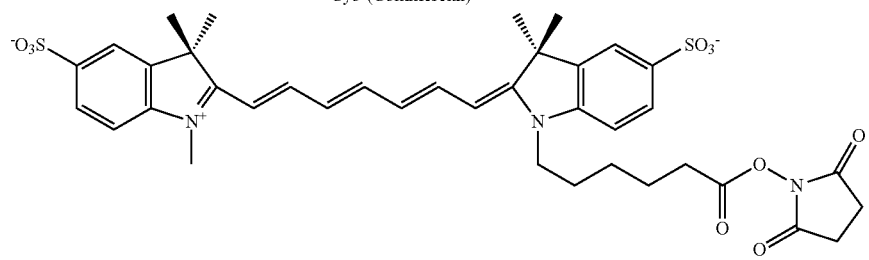

Cy7 (Commercial)

However, since the succinimidyl ester groups are unstable in aqueous solutions, the dyes cannot be maintained stably for a long reaction time. Also, there is a problem that N-hydroxysuccinimide is necessarily produced as a byproduct.

SUMMARY

Technical Problem

The present disclosure is directed to providing a compound for labeling a substance, which is remarkably improved in terms of fluorescing performance, reaction time for binding with biomolecules, production of byproducts after reaction due to detachment of a leaving group, stability in aqueous solutions, especially pH stability and thermal stability, photobleaching or quenching in aqueous solutions or under hydrophilic conditions, molar extinction coefficient, fluorescence wavelength range, etc., and allows staining in various buffers, a method for preparing the same, and a biomolecule or other substance comprising the compound. In particular, the present disclosure is directed to providing a novel benzin- -continued

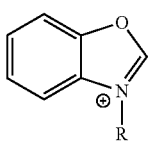

Benzoxazole

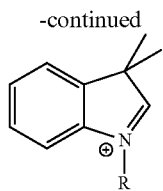

Indole

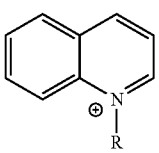

Quinoline

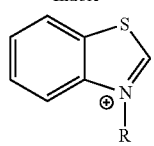

Benzothiazole docyanine compound which may be widely used to identify biomolecules such as proteins, fats or carbohydrates in the field of proteomics, optical molecular imaging, etc., is stable in aqueous solutions and produces no byproducts upon reaction with biomolecules, and a method for preparing the same.

Technical Solution

In an aspect, the present disclosure provides a novel benzindocyanine compound represented by Chemical Formula 1 and a method for preparing the same.

Chemical Formula 1:

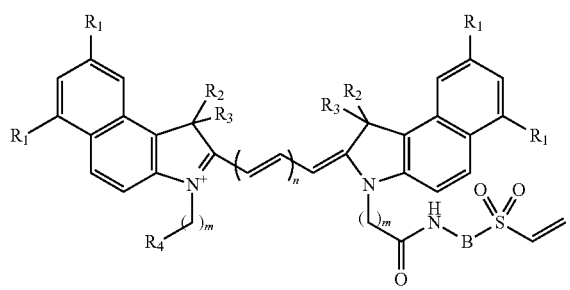

In Chemical Formula 1, each of the four $R_1$'s, which are identical or different, is independently hydrogen, a sulfonic acid group or a sulfonate group;

each of the two $R_2$'s, which are identical or different, is independently hydrogen or a $C_1$-$C_6$ alkyl group;

each of the two $R_3$'s, which are identical or different, is independently hydrogen or a $C_1$-$C_6$ alkyl group;

the $R_4$ is hydrogen, a $C_1$-$C_6$ alkyl group, a carboxyl group, a sulfonic acid group, a sulfonate group, —CONH$(CH_2)_{L1}SO_2CH$=$CH_2$, —CONH-p-$(C_6H_4)SO_2CH$=$CH_2$ or —CONH-m-$(C_6H_4)SO_2CH$=$CH_2$, wherein L1 is an integer from 1 to 5;

the B is $(CH_2)_{L2}$, p-$(C_6H_4)$ or m-$(C_6H_4)$, wherein L2 is an integer from 1 to 5;

the n is an integer from 1 to 5; and each of the two m's, which are identical or different, is independently an integer from 1 to 10, specifically an integer from 1 to 8, most specifically an integer from 1 to 7.

In an exemplary embodiment, the compound for labeling a substance of present disclosure is selected from a group consisting of the following compounds and salts thereof:

1-1

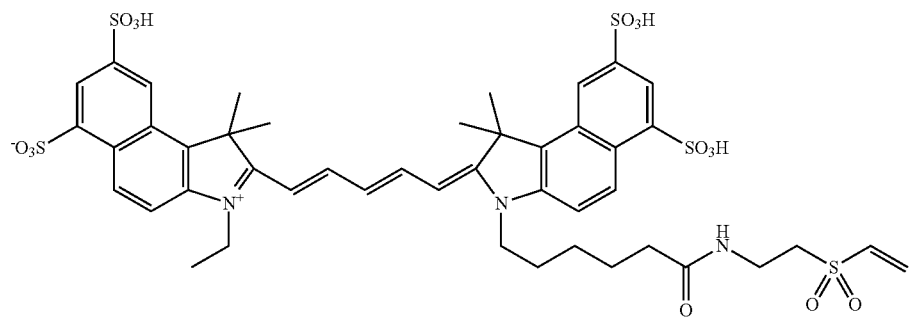

1-2

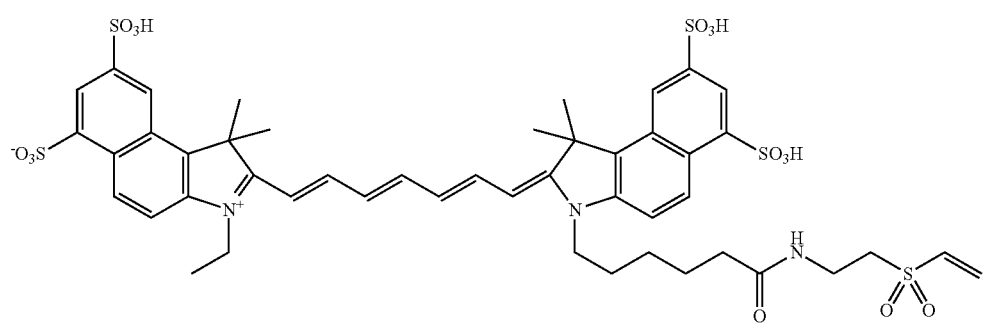

1-3

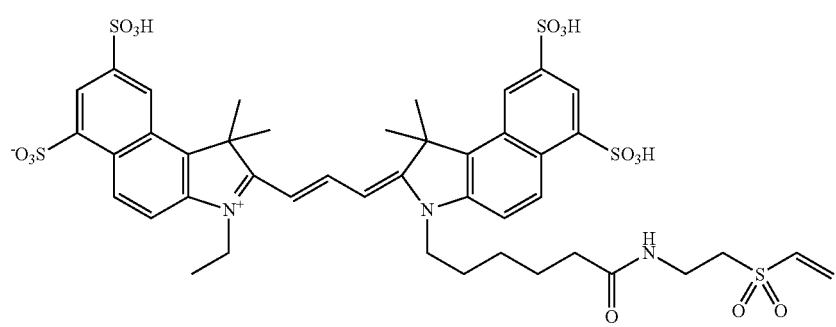

-continued

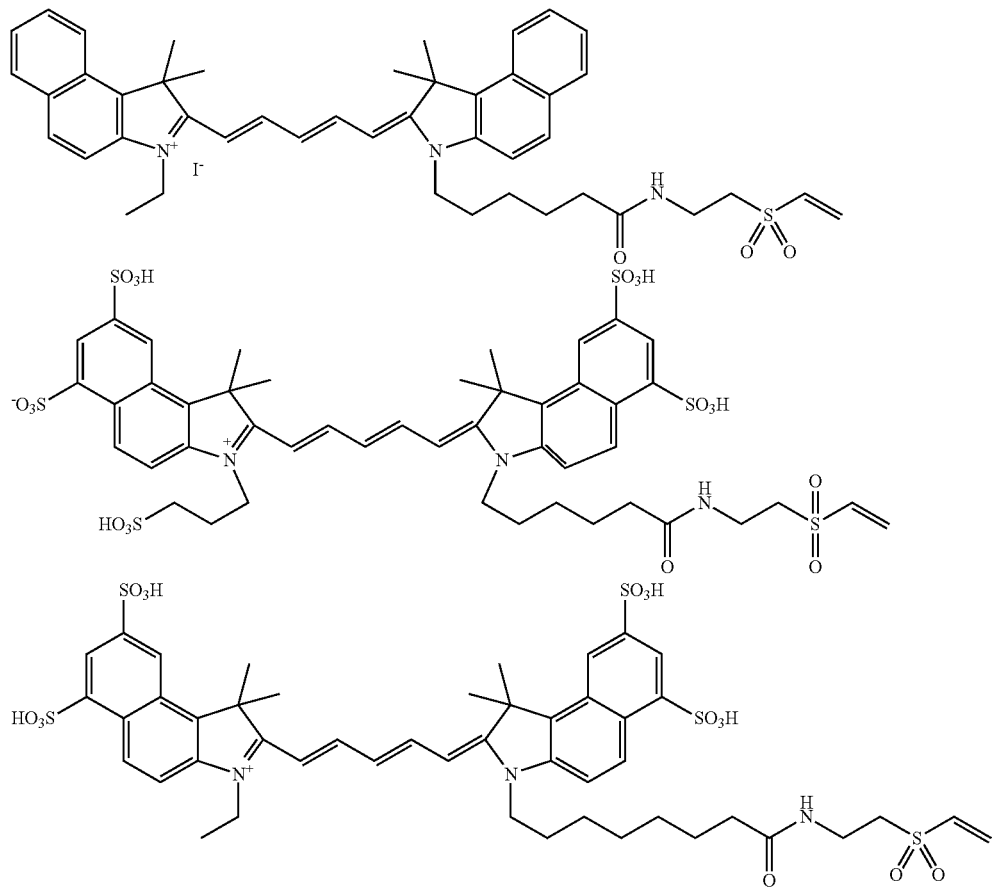

In another exemplary embodiment, the fluorescence wavelength range of the compound for labeling a substance of the present disclosure is 500-800 nm. In another exemplary embodiment, the compound for labeling a substance of the present disclosure is labeled at a biomolecule, a nanoparticle or an organic compound having an amino group, a hydroxyl group or a thiol group. Examples of the biomolecule include protein, peptide, carbohydrate, sugar, fat, antibody, proteoglycan, glycoprotein and siRNA, but are not limited thereto.

In another aspect, the present disclosure provides a method for labeling a substance using the compound for labeling a substance of the present disclosure, wherein the substance is a biomolecule, a nanoparticle or an organic compound having an amino group, a hydroxyl group or a thiol group. In an exemplary embodiment, the labeling of the substance is achieved via binding between a vinyl sulfone group of the compound for labeling a substance of the present disclosure and the amino group, hydroxyl group or thiol group of the biomolecule, nanoparticle or organic compound. In another exemplary embodiment, a buffer selected from a group consisting of phosphate buffer, carbonate buffer and Tris buffer, an organic solvent selected from a group consisting of dimethyl sulfoxide, dimethylformamide and acetonitrile, or water is used as a solvent.

In another exemplary embodiment, the labeling is achieved at pH 5-12. In another exemplary embodiment, the labeling is achieved by reacting the compound for labeling a substance of the present disclosure with the biomolecule, nanoparticle or organic compound at 20-80° C. for 0.5-48 hours. In another aspect, the present disclosure provides a substance selected from a group consisting of a biomolecule, a nanoparticle and an organic compound, which is labeled with the compound for labeling a substance of the present disclosure.

In another aspect, the present disclosure provides a compound represented by Chemical Formula 10, which is an intermediate for preparing the compound for labeling a substance of the present disclosure.

Chemical Formula 10:

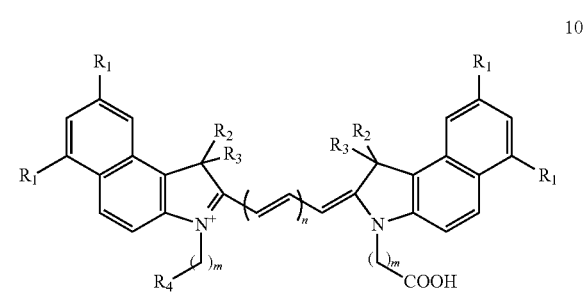

In Chemical Formula 10, each of the four $R_1$'s, which are identical or different, is independently hydrogen, a sulfonic acid group or a sulfonate group; each of the two $R_2$'s, which are identical or different, is independently hydrogen or a $C_1$-$C_6$ alkyl group; each of the two $R_3$'s, which are identical or different, is independently hydrogen or a $C_1$-$C_6$ alkyl group; the $R_4$ is hydrogen, a $C_1$-$C_6$ alkyl group, a carboxyl group, a sulfonic acid group or a sulfonate group; the n is an integer from 1 to 5; and each of the two m's, which are identical or different, is independently an integer from 1 to 10.

In another aspect, the present disclosure provides a method for preparing a benzindocyanine compound represented by Chemical Formula 1, comprising:

(1) reacting a compound represented by Chemical Formula 4 with a compound represented by Chemical Formula 5 or 7 to obtain a compound represented by Chemical Formula 6a;

Chemical Formula 4:

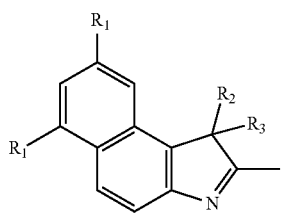

4

Chemical Formula 5:

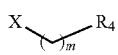

5

Chemical Formula 6a:

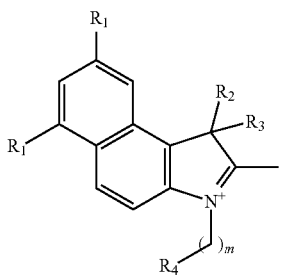

6a

Chemical Formula 7:

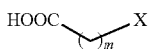

7

(2) reacting the compound represented by Chemical Formula 6a with a compound represented by Chemical Formula 8 to obtain a compound represented by Chemical Formula 9;

Chemical Formula 8:

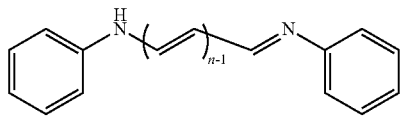

8

Chemical Formula 9:

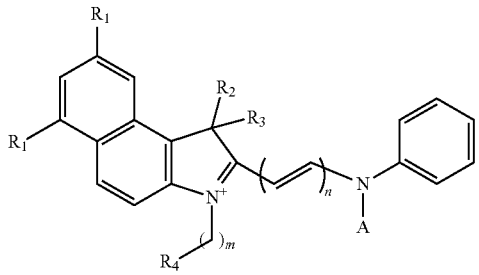

9

(3) reacting the compound represented by Chemical Formula 9 with a compound represented by Chemical Formula 6b to obtain a compound represented by Chemical Formula 10;

Chemical Formula 6b:

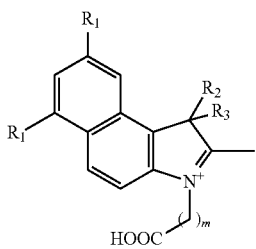

6b

Chemical Formula 10:

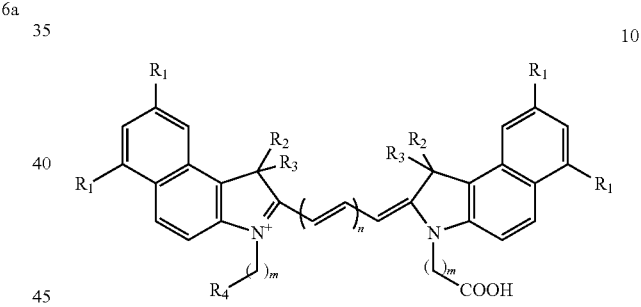

10

(4) reacting the compound represented by Chemical Formula 10 with 1,1'-carbonyldiimidazole or N,N-disuccinimidyl carbonate to obtain a compound represented by Chemical Formula 11a or 11b; and Chemical Formula 11a:

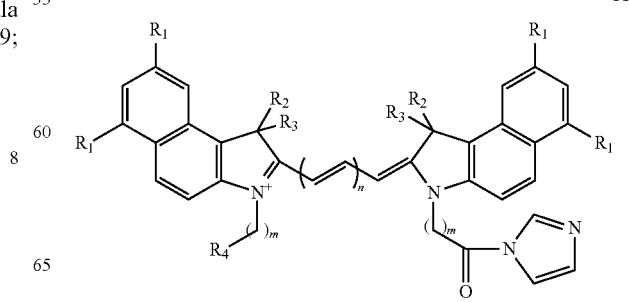

11a

Chemical Formula 11b:

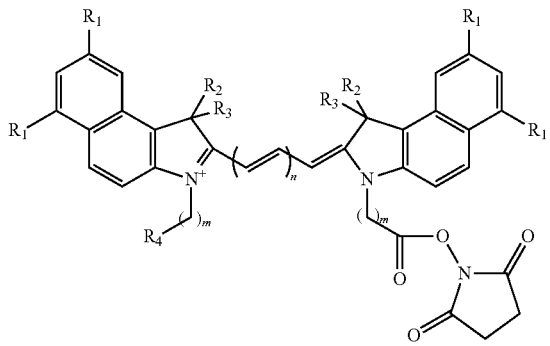

(5) reacting the compound represented by Chemical Formula 11a or 11b with a compound represented by Chemical Formula 12 in the presence of a Hünig's base to obtain a compound represented by Chemical Formula 1:

Chemical Formula 12:

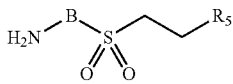

Chemical Formula 1:

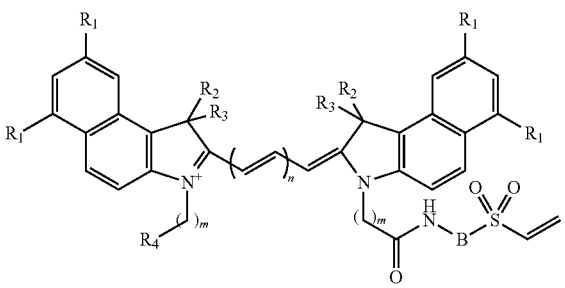

wherein each of the four $R_1$'s, which are identical or different, is independently hydrogen, a sulfonic acid group or a sulfonate group;

each of the two $R_2$'s, which are identical or different, is independently hydrogen or a $C_1$-$C_6$ alkyl group;

each of the two $R_3$'s, which are identical or different, is independently hydrogen or a $C_1$-$C_6$ alkyl group;

the $R_4$ is hydrogen, a $C_1$-$C_6$ alkyl group, a carboxyl group, a sulfonic acid group, a sulfonate group, —CONH($CH_2$)$_{L1}$$SO_2$CH=$CH_2$, —CONH-p-($C_6H_4$)$SO_2$CH=$CH_2$ or —CONH-m-($C_6H_4$)$SO_2$CH=$CH_2$, wherein L1 is an integer from 1 to 5;

the $R_5$ is a halogen atom selected from a group consisting of fluorine, chlorine, bromine and iodine or a sulfato group (—$OSO_3H$);

the A is hydrogen or an acetyl group;

the X is a halogen atom selected from a group consisting of fluorine, chlorine, bromine and iodine;

the B is ($CH_2$)$_{L2}$, p-($C_6H_4$) or m-($C_6H_4$), wherein L2 is an integer from 1 to 5;

the n is an integer from 1 to 5; and each of the two m's, which are identical or different, is independently an integer from 1 to 10.

In another aspect, the present disclosure provides a method for labeling a biomolecule, a nanoparticle or an organic compound with the compound represented by Chemical Formula 1 in various solvents including, for example, buffer. The compound for labeling a substance according to the present disclosure may be widely used to identify biomolecules such as proteins, fats or carbohydrates in the field of proteomics, optical molecular imaging, etc.

Advantageous Effects

The present disclosure allows the biomolecule researchers to more stably manipulate dyes during labeling experiments and, in particular, avoids additional purification since no byproduct is formed after binding between a biomolecule and a dye. With high stability, the compound of the present disclosure can be stored easily for a long period of time and is more effectively applicable to long-term staining of high-molecular-weight or complex biomolecules. Also, the compound for labeling a substance of the present disclosure is remarkably improved in terms of fluorescing performance, reaction time for binding with biomolecules, production of byproducts after reaction due to detachment of a leaving group, stability in aqueous solutions, especially pH stability and thermal stability, photobleaching or quenching in aqueous solutions or under hydrophilic conditions, molar extinction coefficient, fluorescence wavelength range, etc., and allows staining in various buffers.

DETAILED DESCRIPTION

Figure 1:
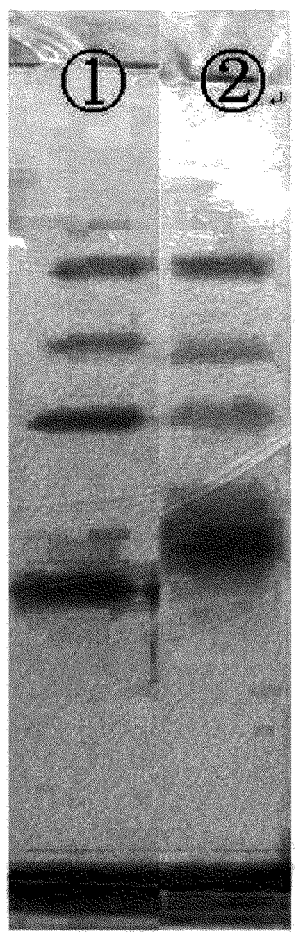
FIG. 1 shows a photographic image of labeled proteins separated by gel electrophoresis.

The present disclosure relates to a benzindocyanine compound represented by Chemical Formula 1. The benzindocyanine compound represented by Chemical Formula 1 according to the present disclosure has a vinyl sulfone group. Since the vinyl group of the vinyl sulfone group binds to a biomolecular nucleophile according to the following reaction, the compound represented by Chemical Formula 1 according to the present disclosure does not form byproducts after reaction with a biomolecule.

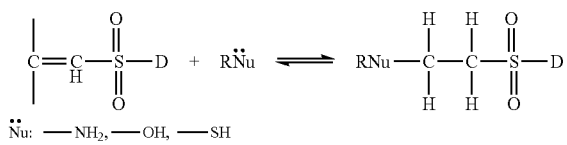

Nu: —$NH_2$, —OH, —SH

R: Biomolecule

D: Dye or Fluorophore

The benzindocyanine dye compound according to the present disclosure is designed for use in water, which is a medium in which most biomolecules are present, and to be stable against heat.

The present disclosure also relates to a novel method for preparing the benzindocyanine compound represented by Chemical Formula 1. The method for preparing the compound represented by Chemical Formula 1 according to the present disclosure will be described hereinbelow.

For preparation of the compound represented by Chemical Formula 1 according to the present disclosure, a compound represented by Chemical Formula 2 is reacted with a compound represented by Chemical Formula 3 as exemplified in Scheme 1 to obtain a compound represented by Chemical Formula 4, which is used as a starting material.

Chemical Formula 2:

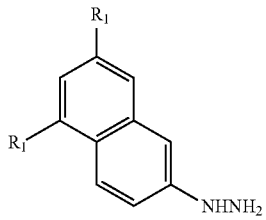

2

Chemical Formula 3:

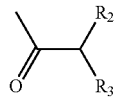

3

Chemical Formula 4:

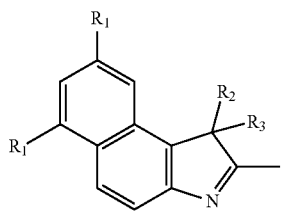

4

Scheme 1

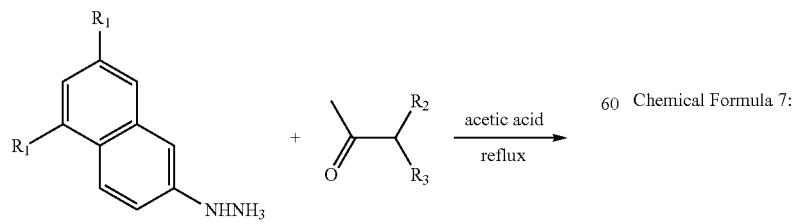

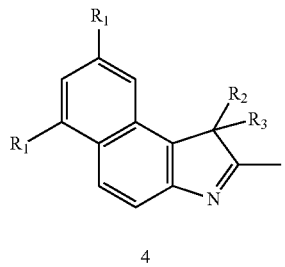

4

In Chemical Formulas 2-4 and Scheme 1, the $R_1$, $R_2$ and $R_3$ are the same as defined in Chemical Formula 1.

In the method for preparing the compound represented by Chemical Formula 1 according to the present disclosure, the compound represented by Chemical Formula 4 is first reacted with a compound represented by Chemical Formula 5 or 7 as exemplified in Schemes 2 and 3 to obtain a compound represented by Chemical Formula 6a or 6b.

Chemical Formula 5:

5

Chemical Formula 6a:

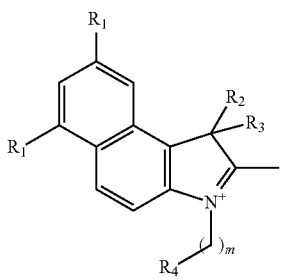

6a

Chemical Formula 6b:

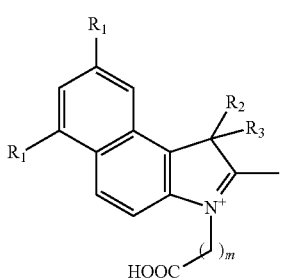

6b

Chemical Formula 7:

7

Scheme 2

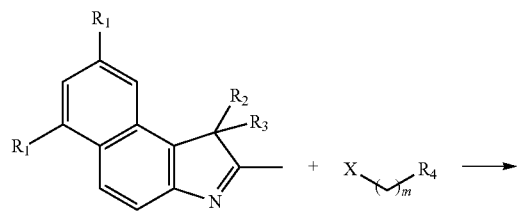

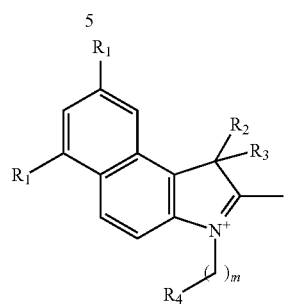

Scheme 3

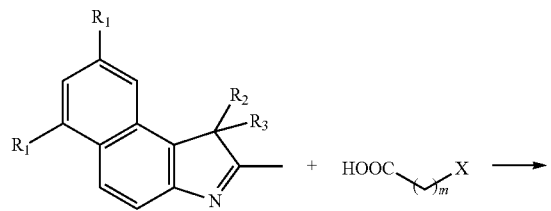

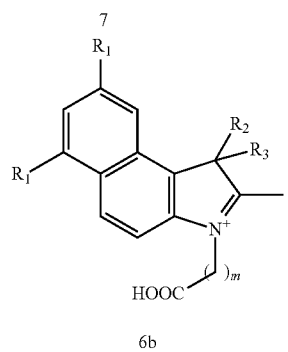

Chemical Formula 8:

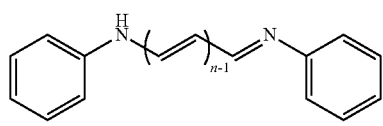

Chemical Formula 9:

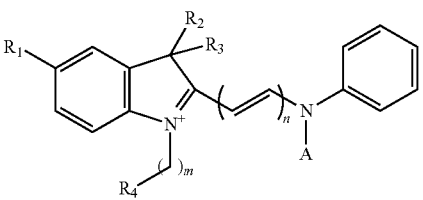

Scheme 4

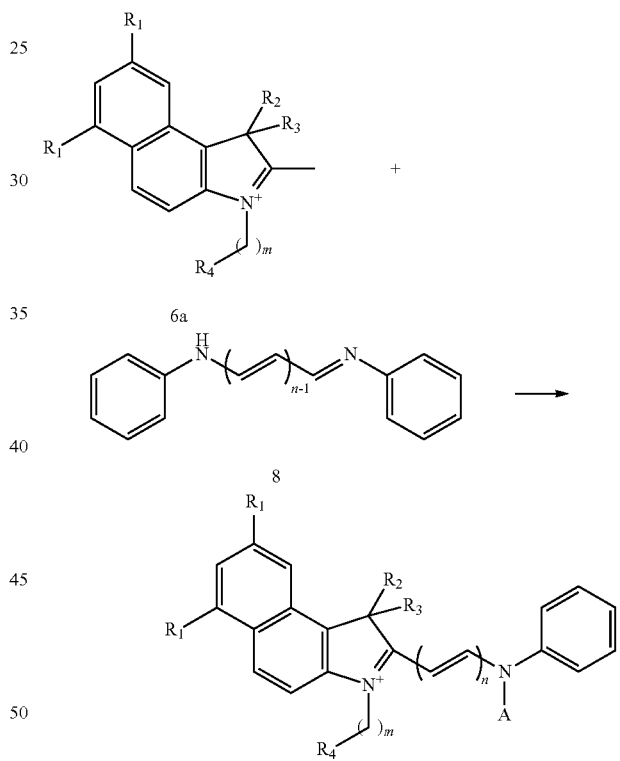

In Chemical Formulas 5-7 and Schemes 2-3, the $R_1$, $R_2$, $R_3$, $R_4$ and m are the same as defined in Chemical Formula 1, and the X is a halogen atom selected from a group consisting of fluorine, chlorine, bromine and iodine.

Scheme 2 exemplifies a procedure of preparing the compound represented by Chemical Formula 6a wherein the $R_4$ is hydrogen or a $C_1$-$C_6$ alkyl group, and Scheme 3 exemplifies a procedure of preparing the compound represented by Chemical Formula 6b wherein the $R_4$ is a carboxyl group. Next, the compound represented by Chemical Formula 6a or 6b is reacted with a compound represented by Chemical Formula 8 as exemplified in Scheme 4 to obtain a compound represented by Chemical Formula 9.

In Chemical Formulas 8-9 and Scheme 4, the $R_1$, $R_2$, $R_3$, $R_4$, m and n are the same as defined in Chemical Formula 1, and the A is hydrogen or an acetyl group. The compound represented by Chemical Formula 8 is N,N-diphenylformamidine (DPF) if n is 1, malonaldehyde dianil hydrochloride (MDH) if n is 2, and glutaconaldehyde dianil hydrochloride (GDH) if n is 3.

Next, the compound represented by Chemical Formula 9 is reacted with a compound represented by Chemical Formula 6b as exemplified in Scheme 5 to obtain a compound represented by Chemical Formula 10.

Chemical Formula 10:

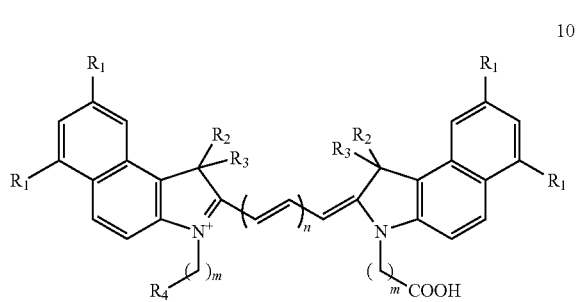

Chemical Formula 11a

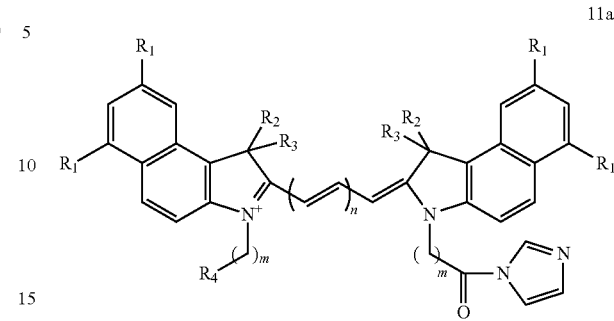

Scheme 5

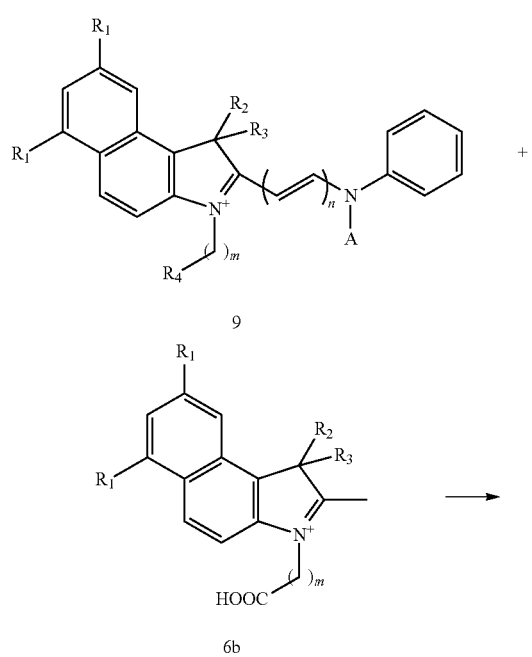

Chemical Formual 11b:

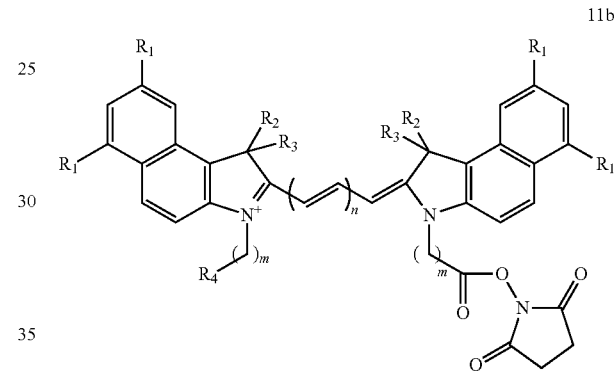

In Chemical Formulas 11a and 11b, the $R_1$, $R_2$, $R_3$, $R_4$, m and n are the same as defined in Chemical Formula 1.

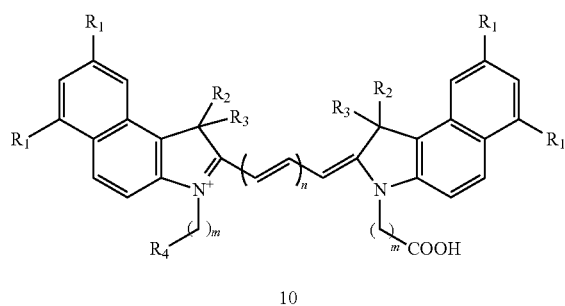

Scheme 6

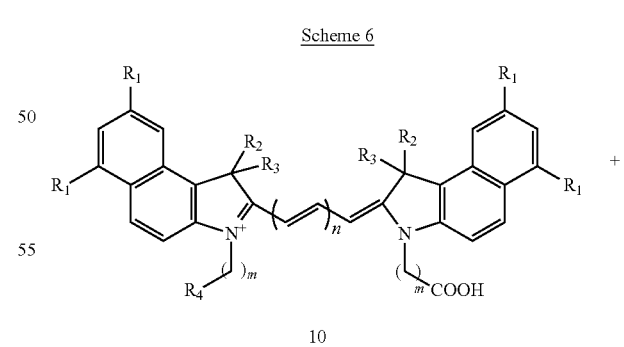

In Chemical Formula 10 and Scheme 5, the $R_1$, $R_2$, $R_3$, $R_4$, m and n are the same as defined in Chemical Formula 1.

Next, the compound represented by Chemical Formula 10 is reacted with 1,1′-carbonyldiimidazole (CD) or N,N-disuccinimidyl carbonate (DSC) as exemplified in Scheme 6 to obtain a compound represented by Chemical Formula 11a or 11b.

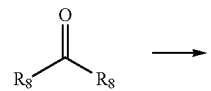

-continued

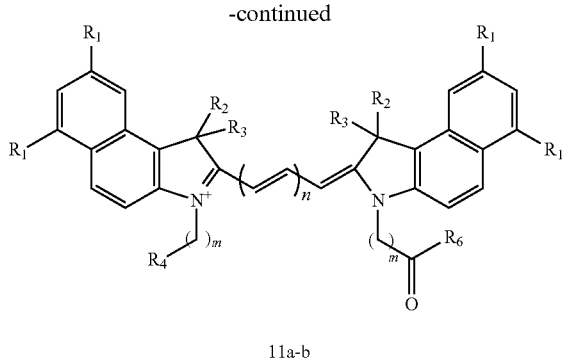

11a-b

In Scheme 6, the $R_1$, $R_2$, $R_3$, $R_4$, m and n are the same as defined in Chemical Formula 1, and the $R_6$ is an imidazole group or a succinimidyloxy group.

Next, the compound represented by Chemical Formula 11a or 11b is reacted with a compound represented by Chemical Formula 12 in the presence of a Hünig's base as exemplified in Scheme 7 to obtain the compound represented by Chemical Formula 1.

Chemical Formula 12:

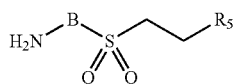

Scheme 7

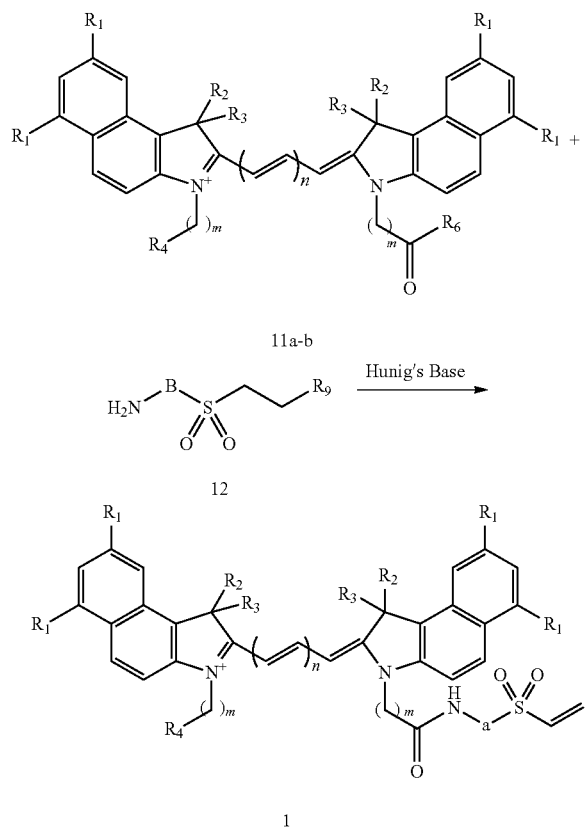

In Chemical Formula 12 and Scheme 7, the $R_1$, $R_2$, $R_3$, $R_4$, m and n are the same as defined in Chemical Formula 1, the $R_5$ is a halogen atom selected from a group consisting of fluorine, chlorine, bromine and iodine or a sulfato group (—$OSO_3H$), the B is ($CH_2$)$_I$, p-($C_6H_4$) or m-($C_6H_4$), and the I is an integer from 1 to 5.

The present disclosure also relates to a method for labeling a biomolecule, a nanoparticle or an organic compound having an amino, hydroxyl or thiol group using the compound represented by Chemical Formula 1. Specifically, the biomolecule is selected from a group consisting of protein, peptide, carbohydrate, sugar, fat, antibody, proteoglycan, glycoprotein and siRNA. The labeling is achieved via binding between a vinyl sulfone group present in the compound represented by Chemical Formula 1 and the amino, hydroxyl or thiol group of the biomolecule, nanoparticle or organic compound. The compound represented by Chemical Formula 1 according to the present disclosure may be easily labeled at a protein via reaction between the protein and the compound represented by Chemical Formula 1, like the existing cyanine dyes having succinimidyl ester groups.

Accordingly, the labeling is achieved using a buffer selected from a group consisting of phosphate buffer, carbonate buffer and Tris buffer, an organic solvent selected from a group consisting of dimethyl sulfoxide, dimethylformamide and acetonitrile, or water as a solvent by reacting the compound represented by Chemical Formula 1 with the biomolecule, nanoparticle or organic compound at pH 5-12. The reaction may be performed at 20-80° C. for 0.5-48 hours.

The present disclosure also relates to a substance selected from a group consisting of a biomolecule, a nanoparticle and an organic compound, which is labeled with the compound represented by Chemical Formula 1. Since a biomolecules is usually already dissolved in a given buffer before packaging and a specific buffer or pH is usually required to ensure stability of the biomolecule, there is a limitation in controlling the variables. Since the compound represented by Chemical Formula 1 according to the present disclosure emits fluorescence by easily reacting with proteins in various buffers under various reaction temperatures and pH conditions, it can be usefully used for labeling of biomolecules.

Hereinafter, the present disclosure will be described in further detail through examples and experiments. However, the following examples are intended only to illustrate the present disclosure and the scope of the present disclosure is not limited thereby.

First, the experimental apparatuses, analytical instruments and reagents used in the examples and experiments are described. Bruker's Avance 300 and 400 were used for FT-NMR spectroscopy, and the Voyager MALDI-TOF DE mass spectrometer was used for MALDI-TOF M/S. Absorption wavelength of the synthesized dye and the absorbance at maximum absorption wavelength were measured using Hewlett-Packard's HP 8452 diode array spectrophotometer. Emission wavelength and light emission at maximum emission wavelength were measured using Perkin Elmer's LS-55.

Column chromatography for separation and purification of organic compounds was carried out using Merck's Kieselgel 60 (230-400 mesh) as silica gel in the case of normal phase. A glass plate coated with Silica gel 60 GF254 (0.25 mm, Merck) was used for thin layer chromatography (TLC). Identification of compounds by TLC was carried out using 254 or 365 nm UV, or a 20-30% phosphomolybdic acid (PMA) ethanol solution or $KMnO_4$ for coloring. In case of reverse phase, a glass plate coated with Silica gel 60 RP-18 F254$_S$ (0.25 mm, Merck) was used for TLC, and column chromatography was carried out using the Lichroprep RP-18 reverse phase column (40-63 μm, Merck) coupled to Buchi's Fraction Collector R-660 as an apparatus for medium pressure liquid chromatography (MPLC). HPLC was carried out using Waters's Bondapak C18 10 μm 125A coupled to Agilent's 1100 series.

Gel electrophoresis was carried out using Bio-Rad's PowerPac Basic Power Supply (Catalog No. 164-5050) coupled to the Amersham Biosciences's SE260 mini-vertical gel electrophoresis unit. Lonza's PAGEr Gold Precast Gels (polyacrylamide gels for protein electrophoresis, 10-20% Trisglycine gels, Catalog No. 59506) were used as gels. Running and loading buffers for SDS-PAGE were prepared as follows prior to use.

Preparation of 5× running buffer
3 g of Tris (Trizma base, Sigma)
14.4 g of glycine (Sigma)
100 mL of distilled water (stored in a refrigerator after preparation)

Preparation of 5× loading buffer
0.6 mL of 1 M Tris (Trizma base, Sigma)
5 mL of 50% glycerol
2 mL of 10% SDS
0.5 mL of 2-mercaptoethanol
1.9 mL of 10% distilled water (instead of bromophenol blue)

Size markers commercially available from GE Healthcare and Takara were used as proteins. Perkin Elmer's Geliance 600 was used for observation of labeled biomolecules and measurement of fluorescence intensity. Geliance UV Epi (Catalog No. L7110026) and Geliance Blue Epi (Catalog No. L7110027) were used as light sources. Measurement was carried out using UV filter, Geliance short-pass filter (500-600 nm), Geliance long-pass filter (580-660 nm) and Geliance blue light filter (550-600 nm) while changing the filters in accordance with fluorescence wavelengths.

Most reagents were purchased from Aldrich and TCI. Solvents requiring purification were purified in accordance with a known method. Unless specified otherwise, all reactions were carried out under nitrogen flow. DMSO-$d_6$ or $D_2O$ available from Aldrich and Cambridge Isotope Laboratories, Inc. were used as NMR solvents. Relative positions of signals were determined based on tetramethylsilane (TMS) in a solvent or based on the NMR solvent. Chemical shift was expressed in ppm unit relative to a standard material, and data were recorded in the order of chemical shift multiplicity (s=singlet, d=doublet, t=triplet, m=multiplet), integration and coupling constant (Hz).

Example 1

Preparation of Compound 1-1

(1) Synthesis of Compound 2-1

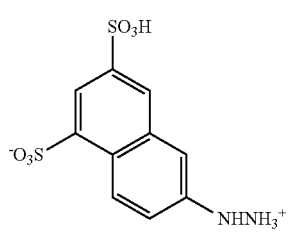

6-Amino-1,3-naphthalene disulfonate disodium salt (10 g, 29 mmol, 1 eq, TCI) was added to 30 mL of water. After complete dissolving, 50 mL of water and 15 mL of strong hydrochloric acid were added. The resulting mixture was cooled to below 0° C. and sodium nitrite (2.2 g, 32 mmol, 1.1 eq) dissolved in 40 mL of water was added for 1 hour. After completely dissolving stannous chloride (11 g, 58 mmol, 2 eq, Aldrich) in 30 mL of water and adding 6 mL of strong hydrochloric acid, the resulting mixture was added to the reaction solution for 20 minutes and stirred overnight at room temperature. After drying the reaction solution under reduced pressure, isopropyl alcohol was added to form particles. The formed particles were filtered, washed using isopropyl alcohol, and dried under reduced pressure (9 g, 97%).

$R_f$=0.95 (RP-C18, methanol/water 3:7 v/v).

(2) Synthesis of Compound 4-1

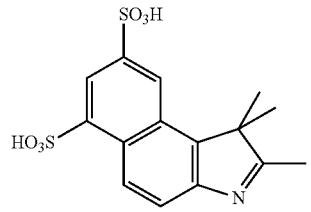

Compound 2-1 (10 g, 25 mmol, 1 eq), isopropyl methyl ketone (12 g, 140 mmol, 5.6 eq) and potassium acetate (6 g, 61 mmol, 2.4 eq) were added together to 75 mL of glacial acetic acid, and the mixture was heated for 24 hours under reflux. The reaction mixture was cooled to room temperature and glacial acetic acid was removed by drying under reduced pressure. The reaction product was completely dissolved in methanol and filtered. The resulting filtrate was concentrated, washed several times with isopropyl alcohol, and dried under reduced pressure (9.6 g, 100%).

$R_f$=0.80 (RP-C18, methanol/water 3:7 v/v).

(3) Synthesis of Compound 6a-1

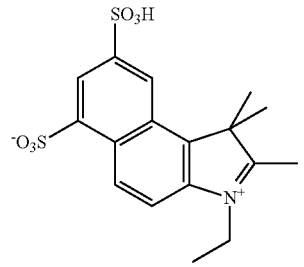

Compound 4-1 (4.6 g, 12.5 mmol, 1 eq) and ethyl iodide (3.6 g, 23 mmol, 1.84 eq) were added to 25 mL of DMF and heated for 24 hours under reflux. After cooling to room temperature and removing ethyl iodide, the reaction mixture was washed 3-4 times with 100 mL of acetone, filtered, and dried at 40° C. under reduced pressure to obtain pink solid (3.6 g, 73%).

$R_f$=0.55 (RP-C18, methanol/water 3:7 v/v).

(4) Synthesis of Compound 6b-1

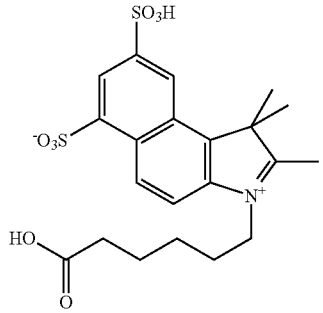

Compound 4-1 (5 g, 13.6 mmol, 1 eq) and 6-bromo-n-hexanoic acid (4.9 g, 25 mmol, 1.84 eq, Aldrich) were heated in 20 mL of 1,2-dichlorobenzene for 12 hours under reflux. After cooling to room temperature, removing the solvent and adding isopropyl alcohol, the mixture was filtered and dried under reduced pressure to obtain pink solid (6.5 g, 98%).

$R_f$=0.60 (RP-C18, methanol/water 3:7 v/v).

(5) Synthesis of Compound 9-1

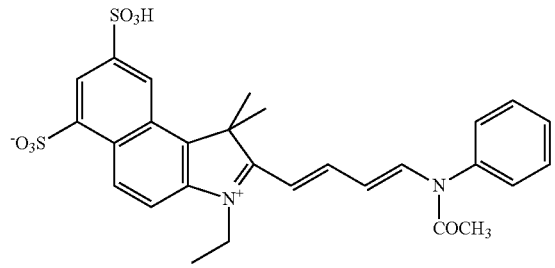

9-1

Compound 6a-1 (6.53 g, 15 mmol, 1 eq) and MDH (4.4 g, 17 mmol, 1.13 eq, TCI) were added to a mixture solution of 30 mL of acetic acid and 30 mL of acetic anhydride. After heating for 4 hours under reflux, the reaction mixture was cooled to room temperature. After removing the solvent, ethyl acetate was added to form particles, which were filtered and dried under reduced pressure to obtain red solid (2.57 g, 30%).

$R_f$=0.48 (RP-C18, methanol/water 3:7 v/v).

(5) Synthesis of Compound 10-1

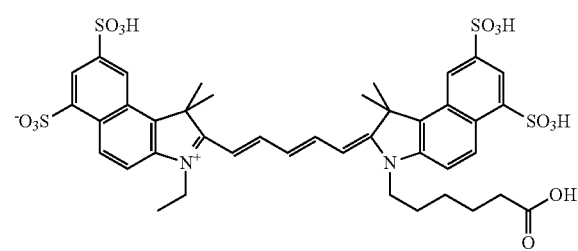

10-1

Compound 9-1 (3.5 g, 11.8 mmol, 1 eq) and Compound 6b-1 (3.08 g, 11.8 mmol, 1 eq) were added to a mixture solution of 30 mL of acetic anhydride and 30 mL of pyridine and reacted at 110° C. for 4 hours. After cooling to room temperature, ethyl acetate was added to form solid, which was filtered and dried under reduced pressure. The product was purified by RP-C18 reverse phase chromatography using 15% methanol aqueous solution as eluent to obtain Compound 10-1 as blue solid (0.54 g, 5%).

$R_f$=0.75 (RP-C18, methanol/water 3:7 v/v).

$^1$H NMR (400 MHz, DMSO-$d_6$): δ 8.98 (t, 2H), 8.43 (t, 4H), 8.23 (s, 2H), 7.72 (d, 2H), 6.62 (t, 1H), 6.35 (d, 2H), 4.38-4.20 (m, 4H), 2.19 (t, 2H), 2.11-1.20 (m, 21H).

MALDI-TOF/MS, calculated $C_{41}H_{45}N_2O_{14}S_4$ 917.17, measured 917.53.

$\lambda_{abs}$ (water): 675 nm, $\lambda_{fl}$ (water): 695 nm.

(6) Synthesis of Compound 1-1

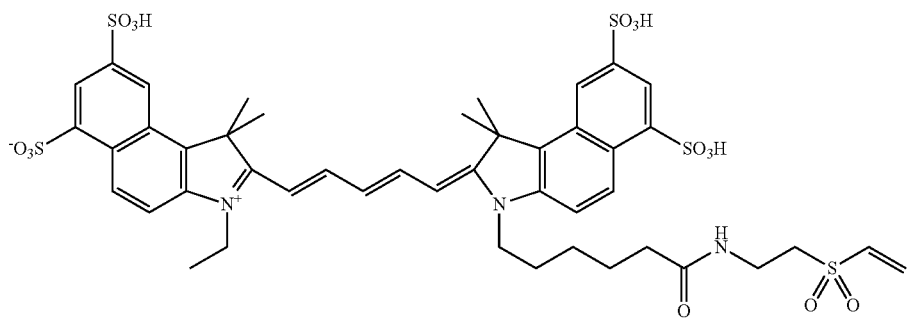

1-1

Compound 10-1 (100 mg, 0.109 mmol, 1 eq) was dissolved in 2 mL of DMF and heated to 60° C. After dissolving in 0.1 mL of pyridine, DSC (81.8 mg, 0.327 mmol, 3 eq) dissolved in 0.8 mL of DMF was added dropwise. After stirring for 1 hour and adding ethyl acetate to precipitate solid, the precipitated green solid was filtered while washing several times with ethyl acetate and ether. After dissolving in 2 mL of DMF and adding 141 mg of Hünig's base, 2-(2'-chloroethylsulfonyl)ethylamine hydrochloride (22.7 mg, 0.109 mmol, 1 eq) dissolved in 0.5 mL of DMF was added dropwise. After stirring at room temperature for at least 12 hours, followed by extraction using water and dichloromethane, the solvent was removed by distillation at 35-40° C. under reduced pressure. The product was purified by RP-C18 reverse phase chromatography using 20% acetonitrile aqueous solution as eluent to obtain Compound 1-1 as blue solid (23 mg, 20%).

$R_f$=0.54 (RP-C18, acetonitrile/water 3:7 v/v).

$^1$H NMR (400 MHz, DMSO-$d_6$): δ 9.02 (t, 2H), 8.45 (m, 4H), 8.21 (s, 2H), 7.72 (m, 2H), 6.97 (m, 1H), 6.65 (t, 1H), 6.52 (t, 1H), 6.38 (d, 2H), 6.26 (m, 1H), 4.17-4.09 (m, 4H), 3.12 (m, 2H), 2.93 (m, 2H), 2.01 (t, 2H, J=7.13 Hz), 1.68-1.23 (m, 21H).

MALDI-TOF/MS, calculated $C_{45}H_{52}N_3O_{15}S_5$ 1034.19, measured 1034.52.

$\lambda_{abs}$ (water): 675 nm, $\lambda_{fl}$ (water): 695 nm.

(1) Synthesis of Compound 9-2

9-2

Compound 1-3 (4.35 g, 10 mmol, 1 eq) and GDH (3.23 g, 11 mmol, 1.1 eq, TCI) was added to 40 mL of acetic anhydride and reacted at 100° C. for 1 hour. After cooling to room temperature and forming solid by adding ethyl acetate, the solid was filtered and dried under reduced pressure (4.96 g, 83%).

$R_f$=0.44 (RP-C18, methanol/water 3:7 v/v).

(2) Synthesis of Compound 10-2

10-2

Compound 9-3 (1.70 g, 2.68 mmol, 1 eq) and Compound 1-4 (1.4 g, 2.68 mmol, 1 eq) were dissolved in 30 mL of pyridine and reacted at 40° C. for 1 hour. After cooling to room temperature and forming green solid by adding ethyl acetate, the solid was filtered and dried under reduced pressure. The product was purified by RP-C18 reverse phase chromatography using 30% acetonitrile aqueous solution as eluent to obtain pure Compound 10-3.

$R_f$=0.54 (RP-C18, methanol/water 3:7 v/v).

$^1$H NMR (400 MHz, DMSO-$d_6$): δ 9.02 (d, 2H), 8.42-8.34 (m, 2H), 8.28 (s, 2H), 8.03 (t, 2H), 7.70 (d, 2H), 6.61 (t, 3H), 6.41 (d, 2H), 4.30-4.11 (m, 4H), 2.02 (t, 2H), 2.11-1.20 (m, 21H).

MALDI-TOF/MS, calculated $C_{43}H_{47}N_2O_{14}S_4$ 942.18, measured 942.68.

$\lambda_{abs}$ (water): 777 nm, $\lambda_{fl}$ (water): 803 nm.

Compound 3-2 (100 mg, 0.106 mmol, 1 eq) was dissolved in 2 mL of DMF and heated to 60° C. After dissolving in 0.1 mL of pyridine, DSC (79.6 mg, 0.318 mmol, 3 eq) dissolved in 0.8 mL of DMF was added dropwise. After stirring for 1 hour and adding ethyl acetate to precipitate solid, the precipitated green solid was filtered while washing several times with ethyl acetate and ether. After dissolving in 2 mL of DMF and adding 137 mg of Hünig's base, 2-(2'-chloroethylsulfonyl)ethylamine hydrochloride (22.1 mg, 0.106 mmol, 1 eq) dissolved in 0.5 mL of DMF was added dropwise and the resulting mixture stirred at room temperature for at least 12 hours. After extracting using water and dichloromethane, the solvent was removed by distillation at 35-40° C. under reduced pressure. The product was purified by RP-C18 reverse phase chromatography using 20% acetonitrile aqueous solution as eluent to obtain pure Compound 3-3.

$R_f$=0.71 (RP-C18, acetonitrile/water 3:7 v/v).

MALDI-TOF/MS, calculated $C_{47}H_{54}N_3O_{15}S_5$ 1060.21, measured 1060.79.

$\lambda_{abs}$ (water): 777 nm, $\lambda_{fl}$ (water): 803 nm.

Example 3

Preparation of Compound 1-3

(1) Synthesis of Compound 9-3

9-3

(3) Synthesis of Compound 1-2

1-2

Compound 1-3 (6.53 g, 15 mmol, 1 eq) and DPF (3.3 g, 17 mmol, 1.13 eq, TCI) were added to a mixture solution of 30 mL of acetic acid and 30 mL of acetic anhydride and heated for 4 hours under reflux. After cooling to room temperature and removing the solvent, ethyl acetate was added to form solid, which was filtered and dried under reduced pressure (4.33 g, 53%).

$R_f$=0.65 (RP-C18, methanol/water 3:7 v/v).

(2) Synthesis of Compound 10-3

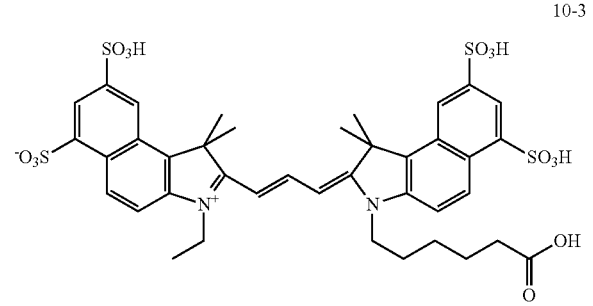

10-3

Compound 1-5 (4.4 g, 7.5 mmol, 1 eq) and Compound 1-4 (3.9 g, 7.5 mmol, 1 eq) were added to a mixture solution of 30 mL of acetic anhydride and 30 mL of pyridine and reacted at 110° C. for 4 hours. After cooling to room temperature and forming solid by adding ethyl acetate, the solid was filtered and dried under reduced pressure. The product was purified by RP-C18 reverse phase chromatography using 15% acetonitrile aqueous solution as eluent to obtain pure Compound 10-1 (0.4 g, 6%).

$R_f$=0.52 (RP-C18, acetonitrile/water 3:7 v/v).

$^1$H NMR (400 MHz, DMSO-d$_6$): δ 9.1 (t, 1H), 8.92-8.74 (m, 4H), 8.43 (m, 2H), 7.76 (d, 2H), 6.24 (d, 2H), 4.03 (m, 4H), 2.45 (t, 2H), 1.99-1.14 (m, 21H).

MALDI-TOF/MS, calculated $C_{39}H_{43}N_2O_{14}S_4$ 891.15, measured 891.51.

$\lambda_{abs}$ (water): 579 nm, $\lambda_{fl}$ (water): 594 nm.

(3) Synthesis of Compound 1-3 hour and precipitating solid by adding ethyl acetate, the precipitated green solid was filtered while washing several times with ethyl acetate and ether. After dissolving in 2 mL of DMF and adding 145 mg of Hünig's base, 2-(2'-chloroethylsulfonyl)ethylamine hydrochloride (23.3 mg, 0.112 mmol, 1 eq) dissolved in 0.5 mL of DMF was added dropwise and stirred at room temperature for at least 12 hours. After extracting using water and dichloromethane, the solvent was removed by distillation at 35-40° C. under reduced pressure. The product was purified by RP-C18 reverse phase chromatography using 20% acetonitrile aqueous solution as eluent to obtain pure Compound 1-7 (12 mg, 12%).

$R_f$=0.58 (RP-C18, acetonitrile/water 3:7 v/v).

MALDI-TOF/MS, calculated $C_{43}H_{50}N_3O_{15}S_5$ 1008.18, measured 1008.69.

$\lambda_{abs}$ (water): 579 nm, $\lambda_{fl}$ (water): 594 nm.

Example 4

Preparation of Compound 1-4

(1) Synthesis of Compound 6a-2

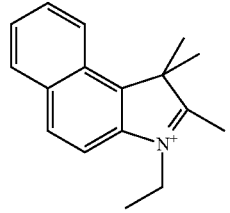

2,3,3-Trimethyl-4,5-benzo-3H-indole (18.75 g, 90 mmol, 1 eq, TCI) and ethyl iodide (36 mL, 450 mmol, 5 eq, TCI) were added to 225 mL of 1,2-dichlorobenzene and heated for 24 hours under reflux. After cooling to room temperature and removing the solvent, the resultant was washed 3-4 times with 1 L of acetone and filtered to remove ethyl iodide. The product was dried at 40° C. under reduced pressure to obtain pink solid (17.1 g, 80%).

$R_f$=0.25 (normal phase, n-propanol/2-butanol/ethyl acetate/water 4:2:1:3 v/v).

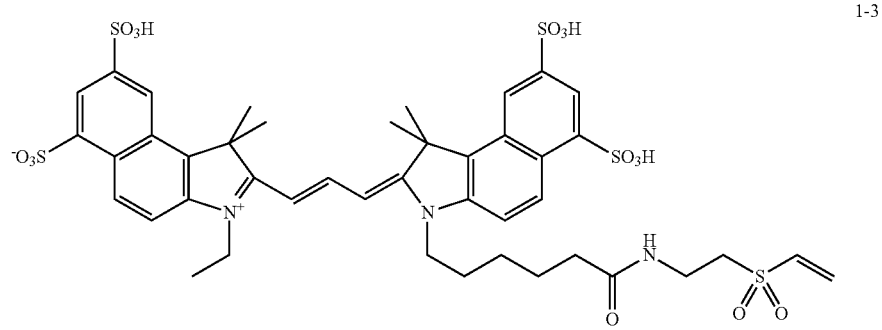

1-3

Compound 3-2 (100 mg, 0.112 mmol, 1 eq) was dissolved in 2 mL of DMF and heated to 60° C. After dissolving in 0.1 mL of pyridine, DSC (84.1 mg, 0.336 mmol, 3 eq) dissolved in 0.8 mL of DMF was added dropwise. After stirring for 1

(2) Synthesis of Compound 6b-2

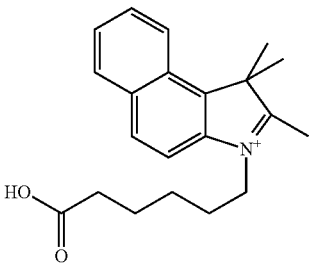

2,3,3-Trimethyl-4,5-benzo-3H-indole (12.5 g, 60 mmol, 1 eq, TCI) and 6-bromo-n-hexanoic acid (23.4 g, 120 mmol, 2 eq, Aldrich) were added to 135 mL of 1,2-dichlorobenzene and heated for 24 hours under reflux. After cooling to room temperature, removing the solvent and adding isopropyl alcohol, the resultant was dried under reduced pressure to obtain white solid (14.9 g, 77%).

$R_f$=0.19 (n-propanol/2-butanol/ethyl acetate/water 4:2:1:3 v/v).

(3) Synthesis of Compound 9-4

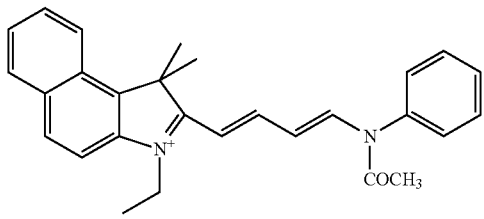

(4) Synthesis of Compound 10-4

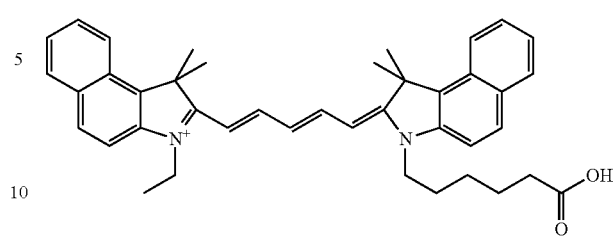

Compound 9-4 (1.3 g, 2.5 mmol, 1 eq) and Compound 6b-2 (1 g, 2.5 mmol, 1 eq) were added to 6.2 mL of pyridine and reacted at 80° C. for 4 hours. After cooling to room temperature and forming solid by adding ethyl acetate, the solid was dried under reduced pressure. The product was purified by normal phase chromatography using methylene chloride, methanol and n-hexane (5:1:1 v/v) as eluent to obtain Compound 10-4 as blue solid (432 mg, 29%).

$R_f$=0.57 (normal phase, methylene chloride/methanol/n-hexane 5:1:1 v/v).

$^1$H NMR (400 MHz, DMSO-d$_6$): δ 8.44 (t, 2H), 8.24 (d, 2H), 8.09-8.03 (m, 4H), 7.73 (d, 2H), 7.69-7.64 (m, 2H), 7.52-7.47 (m, 2H), 6.63 (t, 1H), 6.38-6.32 (m, 2H), 4.27-4.21 (m, 4H), 2.12 (t, 2H), 1.95-1.30 (m, 21H).

LC/MS, calculated $C_{41}H_{45}N_2O_2$ 597.35, measured 597.16.

$\lambda_{abs}$ (methanol): 697 nm, $\lambda_{fl}$ (methanol): 713 nm.

(5) Synthesis of Compound 1-4

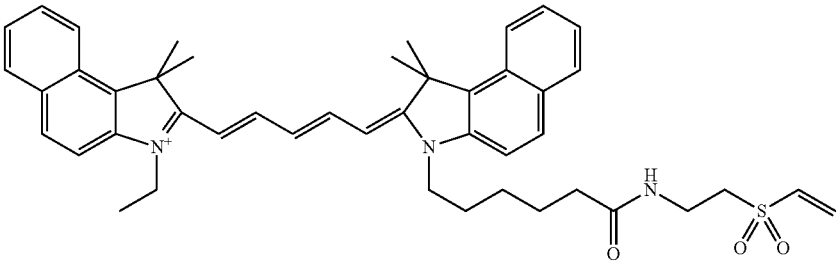

Compound 6a-2 (5 g, 21 mmol, 1 eq) and MDH (5 g, 21 mmol, 1 eq, TCI) were added to a mixture solution of 25 mL of acetic acid and 25 mL of acetic anhydride and heated for 4 hours under reflux. After cooling to room temperature and forming particles by adding ethyl acetate, the particles were filtered and dried under reduced pressure to obtain red solid (4.2 g, 49%).

$R_f$=0.58 (normal phase, n-propanol/2-butanol/ethyl acetate/water 4:2:1:3 v/v).

Compound 10-4 (240 mg, 0.44 mmol, 1 eq) was dissolved in 10 mL of DMF and heated to 60° C. After adding 0.44 mL of pyridine dropwise, DSC (225 mg, 0.76 mmol, 1.7 eq, Aldrich) dissolved in 2 mL of DMF was added dropwise. After stirring for 1 hour and precipitating solid by adding ethyl acetate, the precipitated solid was filtered while washing several times with ethyl acetate and ether. After dissolving in 10 mL of DMF and adding 0.42 µL of Hünig's base, 2-(2'-chloroethylsulfonyl)ethylamine hydrochloride (130 mg, 0.48 mmol, 1 eq) dissolved in 1 mL of DMF was added dropwise and the mixture was stirred at room temperature for at least 12 hours. After extracting using water and dichloromethane, the solvent was removed by distillation at 35-40° C. under reduced pressure. The produced was purified by NP silica gel chromatography using n-propanol, 2-butanol, ethyl acetate and water (4:2:1:3 v/v) as eluent to obtain Compound 1-4 as solid (27 mg, 7.9%).

$R_f$=0.59 (NP silica gel, n-propanol/2-butanol/ethyl acetate/water 4:2:1:3 v/v).

$^1$H NMR (400 MHz, DMSO-$d_6$): δ 8.45 (t, 2H), 8.24 (d, 2H), 8.09-8.00 (m, 4H), 7.75-7.72 (m, 2H), 7.69-7.65 (m, 2H), 7.52-7.48 (m, 2H), 6.99-6.93 (m, 1H), 6.63 (t, 1H), 6.37-6.33 (m, 2H), 6.25-6.21 (m, 2H), 4.28-4.21 (m, 4H), 3.36-3.33 (m, 2H), 3.23-3.12 (m, 2H), 2.05 (m, 2H), 1.96-1.30 (m, 21H).

LC/MS, calculated $C_{45}H_{52}N_3O_3S$ 714.37, measured 714.7.

$\lambda_{abs}$ (methanol): 680 nm, $\lambda_{fl}$ (methanol): 710 nm.

Example 5
Preparation of Compound 1-5

(1) Synthesis of Compound 6b-3

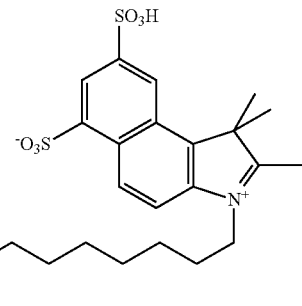

Compound 4-1 (5 g, 13.6 mmol, 1 eq) and 8-bromo-n-octanoic acid (5.6 g, 25 mmol, 1.84 eq, TCI) were heated in 20 mL of 1,2-dichlorobenzene for 12 hours under reflux. After cooling to room temperature, removing the solvent and adding isopropyl alcohol, the resultant was filtered and dried under reduced pressure to obtain pink solid (5.9 g, 82%).

$R_f$=0.52 (RP-C18, methanol/water 3:7 v/v).

(2) Synthesis of Compound 10-5

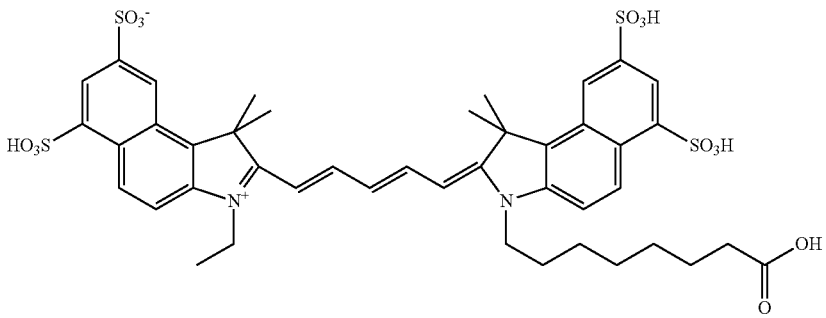

Compound 9-1 (2.3 g, 4 mmol, 1 eq) and Compound 6b-3 (3.6 g, 7 mmol, 1.8 eq) were added to 30 mL of pyridine and reacted at 100° C. for 30 minutes. After cooling to room temperature and forming solid by adding ethyl acetate, the solid was filtered and dried under reduced pressure. The product was purified by RP-C18 reverse phase chromatography using 18% acetonitrile aqueous solution as eluent to obtain Compound 10-5 as blue solid (0.52 g, 14%).

$R_f$=0.6 (RP-C18, acetonitrile/water 2.5:7.5 v/v).

$^1$H NMR (400 MHz, DMSO-$d_6$): δ 8.90-8.88 (m, 2H), 8.43 (s, 2H), 8.19 (s, 2H), 8.02-7.99 (m, 2H), 7.73 (d, 2H), 6.63 (t, 1H), 6.38-6.34 (d, 2H), 4.30-4.11 (m, 4H), 2.02 (t, 2H), 2.11-1.20 (m, 25H).

$\lambda_{abs}$ (water): 675 nm, $\lambda_{fl}$ (water): 704 nm.

(3) Synthesis of Compound 1-5

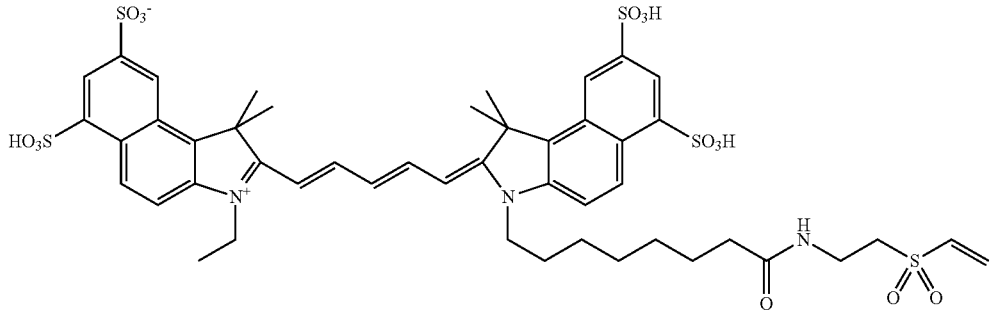 [SMILES: C=CS(=O)(=O)CCNC(=O)CCCCCCCN1/C(=C/C=C/C=C/C2=[N+](CC)c3ccc4c(S(=O)(=O)O)cc(S(=O)(=O)O)cc4c3C2(C)C)C(C)(C)c2c1ccc1c(S(=O)(=O)O)cc(S(=O)(=O)O)cc21]

Compound 10-5 (500 mg, 0.53 mmol, 1 eq) was dissolved in 25 mL of DMF and heated to 60° C. After adding 450 μL of Hünig's base dropwise, DSC (696 mg, 628 mg, 2.12 mmol, 4 eq, Aldrich) dissolved in 3 mL of DMF was added dropwise. After stirring for 1 hour and precipitating solid by adding ethyl acetate, the precipitated green solid was filtered while washing several times with ethyl acetate and ether. After dissolving in 25 mL of DMF and adding 450 μL of Hünig's base, 2-(2'-chloroethylsulfonyl)ethylamine hydrochloride (141 mg, 0.53 mmol, 1 eq) dissolved in 3 mL of DMF was added dropwise and the resulting mixture was stirred at room temperature for at least 12 hours. After extracting using water and dichloromethane, the solvent was removed by distillation at 35-40° C. under reduced pressure. The product was purified by RP-C18 reverse phase chromatography using 16% acetonitrile aqueous solution as eluent to obtain Compound 1-5 as blue solid (260 mg, 44%).

$R_f$=0.58 (RP-C18, acetonitrile/water 2.5:7.5 v/v).

$^1$H NMR (400 MHz, DMSO-$d_6$): δ 9.02 (m, 2H), 8.43 (s, 2H), 8.18 (s, 2H), 7.96 (t, 1H), 7.75-7.72 (m, 2H), 6.98-6.92 (m, 1H), 6.62 (t, 1H), 6.52 (t, 1H), 6.38-6.33 (m, 2H), 6.23-6.20 (m, 2H), 4.17-4.10 (m, 4H), 3.62-3.58 (m, 2H), 3.14-3.11 (m, 2H), 2.01 (t, 2H), 1.94-1.20 (m, 25H).

LC/MS, calculated $C_{47}H_{55}N_3O_{15}S_5$ 1061.22, measured 1061.41.

$\lambda_{abs}$ (water): 675 nm, $\lambda_{fl}$ (water): 704 nm.

Example 6

Staining of Proteins

Each vial of one pack of Amersham™ LMW calibration kit (17-0446-01) for SDS electrophoresis commercially available from GE Healthcare contains 576 μg of six marker proteins, which are phosphorylase b (97 kD, 67 μg), albumin (66 kD, 83 μg), ovalbumin (45 kD, 147 μg), carbonic anhydrase (30 kD, 83 μg), trypsin inhibitor (20.1 kD, 80 μg) and α-lactalbumin (14.4 kD, 116 μg). 250 μL of 0.1 M phosphate buffer (pH 9.0) was added at room temperature (20° C.) to the vial containing the marker proteins to dissolve the proteins and 25 μL of aliquots were obtained in two e-tubes (25 μg protein/25 μL buffer, 6.9×10$^{-5}$ μmol in 25 μL buffer solution). Compounds 1-1 and 1-2 (1 mg each) were respectively added to an e-tube and dissolved by adding 100 μL of DMF. Each 1 μL of the resulting solution was added to each of the e-tubes containing the proteins. The resulting mixture was homogeneously mixed using a vortex shaker and a centrifuge and reaction was proceeded at room temperature for 1 hour.

After adding 6 μL of 5× loading buffer to the reaction solution, 15 μL was taken and separated by gel electrophoresis. The result is shown in FIG. 1. The electrophoresis was carried out at 125 V for 2 hours. FIG. 1 shows fluorescence images (①: Compound 1-1, ②: Compound 1-2). The stained proteins are discernible with naked eyes.

Example 7

Peptide Labeling and In Vivo Molecular Imaging

Apopep-1 (sequence: CQRPPR, molecular weight: 740.88, Peptron, Korea) known as a peptide capable of detecting necrotic cells and tumor cells was used. 4 mM Apopep-1 was dissolved in DMSO together with GE Healthcare's Cy7.5 or Compound 1-2 of equal equivalence (1 mg/100 μL) and reacted in DMSO solvent at room temperature for 12 hours. Each labeled peptide was prepared into a 50 μM solution using PBS buffer.

Two nude mice were tumor-xenotransplanted using MDA231 tumor cells. The peptide labeled with Cy7.5 or Compound 1-2 was injected into the tail vein of each mouse to a final concentration of 50 μM under isoflurane anesthesia. 30 minutes later, in vivo fluorescence image was obtained using Optix exPlore (GE Healthcare). Each image was normalized using the software provided with the instrument.

Figure 2:
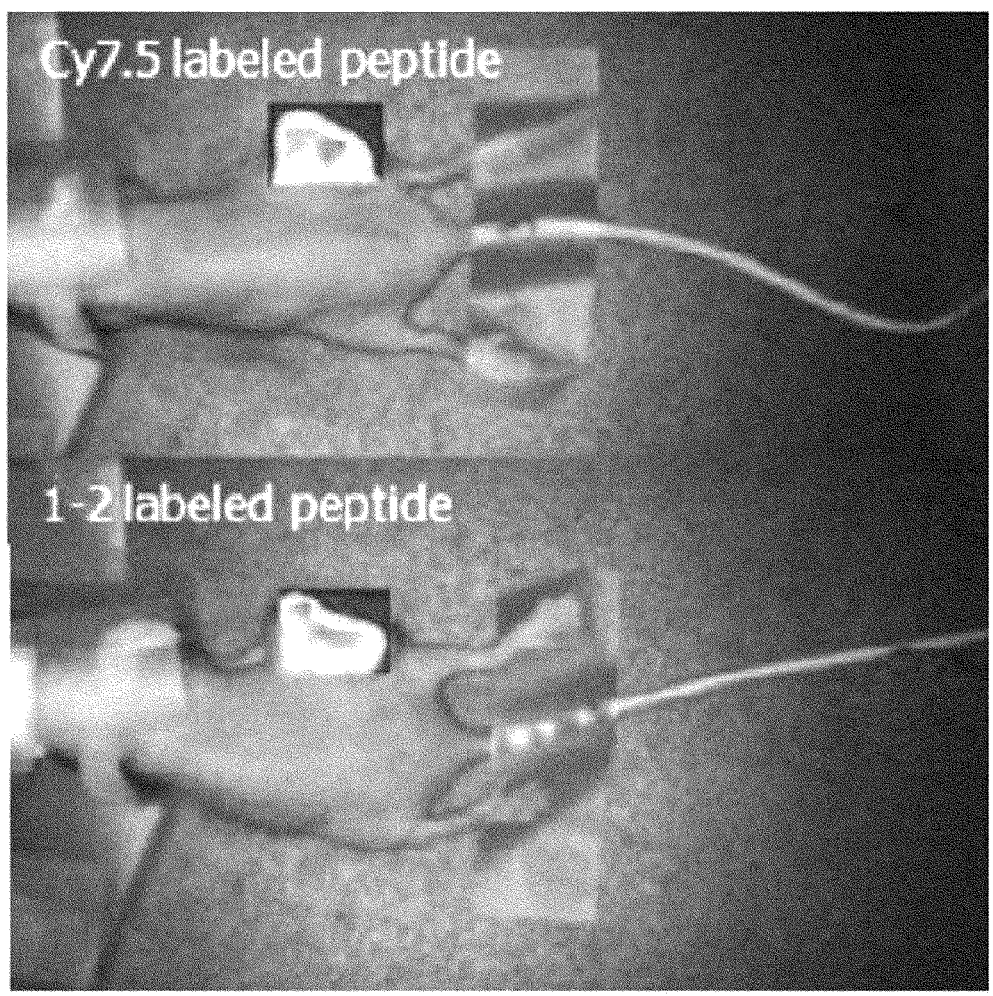
FIG. 2 shows a result of injecting peptides labeled respectively with Cy7.5 and Compound 1-2 into the blood vessels of tumor-xenotransplanted nude mice and imaging in vivo targets using fluorescence.

As seen from FIG. 2, fluorescence was observed in the tumor-xenotransplanted regions. The fluorescence intensity did not decrease after the labeling, suggesting that the labeling does not negatively affect the peptide's ability of detecting tumors. As demonstrated through the foregoing examples, the compound according to the present disclosure is remarkably improved in terms of fluorescing performance, reaction time for binding with biomolecules, production of byproducts after reaction due to detachment of a leaving group, stability in aqueous solutions, especially pH stability and thermal stability, photobleaching or quenching in aqueous solutions or under hydrophilic conditions, molar extinction coefficient, fluorescence wavelength range, etc., and allows staining in various buffers.

The reaction schemes and conditions of the present disclosure are applicable also to the compounds that are within the scope of the present disclosure but have functional groups not explicitly described in the examples, although the compounds may exhibit different physical properties depending on the kind and structure of the functional groups. Accordingly, it is obvious that those skilled in the art may easily test the compounds of the present disclosure not explicitly described in the examples based on the description of the present disclosure and common knowledge at the time of application of the present disclosure.

The invention claimed is:

1. A benzindocyanine compound represented by Chemical Formula 1 or a salt thereof:

Chemical Formula 1:

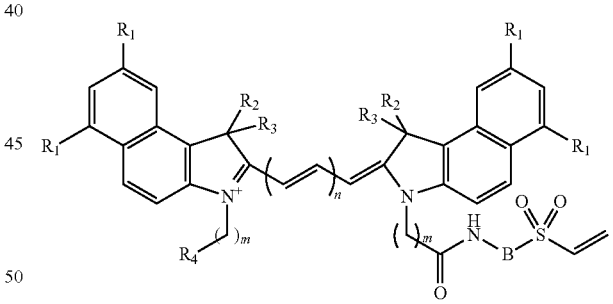

wherein
each of the four $R_1$'s, which are identical or different, is independently hydrogen, a sulfonic acid group or a sulfonate group;
each of the two $R_2$'s, which are identical or different, is independently hydrogen or a $C_1$-$C_6$ alkyl group;
each of the two $R_3$'s, which are identical or different, is independently hydrogen or a $C_1$-$C_6$ alkyl group;
the $R_4$ is hydrogen, a $C_1$-$C_6$ alkyl group, a carboxyl group, a sulfonic acid group, a sulfonate group, —CONH$(CH_2)_{L1}SO_2CH$═$CH_2$, —CONH-p-($C_6H_4$)$SO_2CH$═$CH_2$ or —CONH-m-($C_6H_4$)$SO_2CH$═$CH_2$, wherein L1 is an integer from 1 to 5;
the B is $(CH_2)_{L2}$, p-($C_6H_4$) or m-($C_6H_4$), wherein L2 is an integer from 1 to 5;

the n is an integer from 1 to 5; and
each of the two m's, which are identical or different, is independently an integer from 1 to 10.
2. The benzindocyanine compound according to claim 1, wherein the compound represented by Chemical Formula 1 is one selected from a group of the following compounds:
1-1
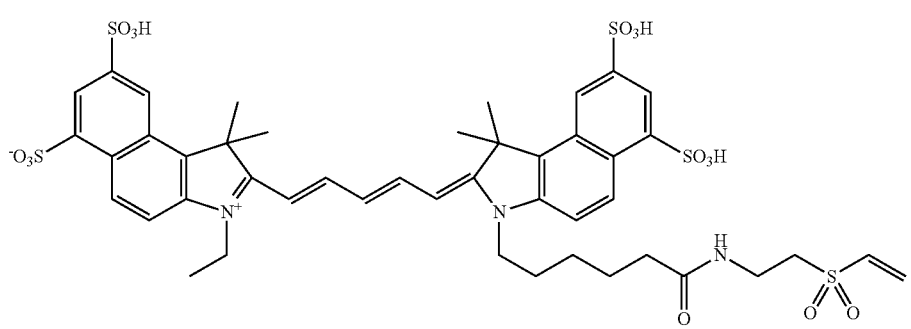
1-2
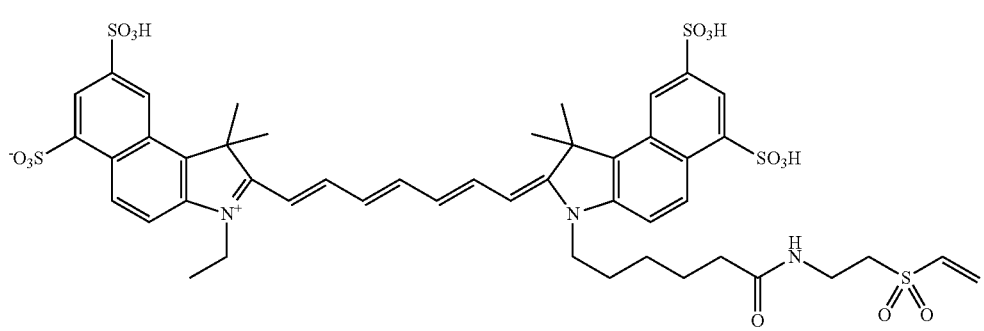
1-3
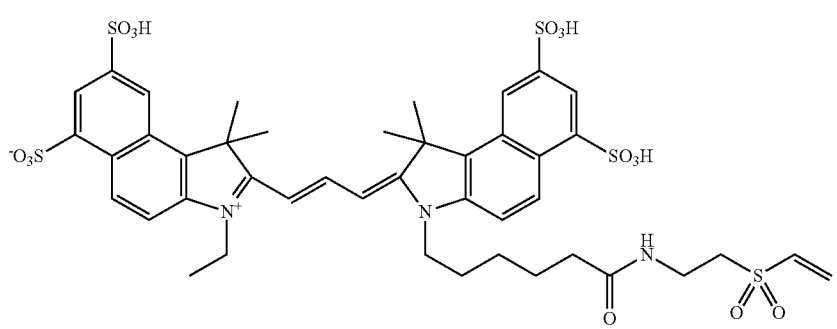
1-4
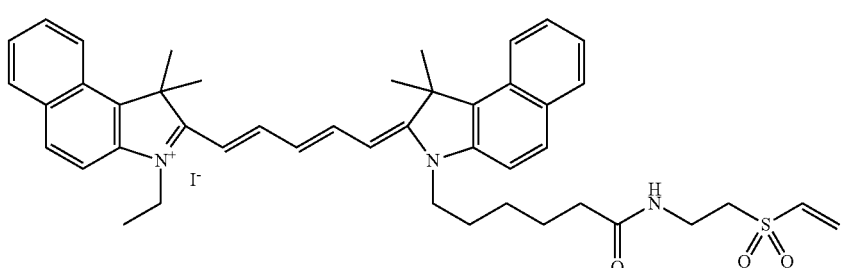
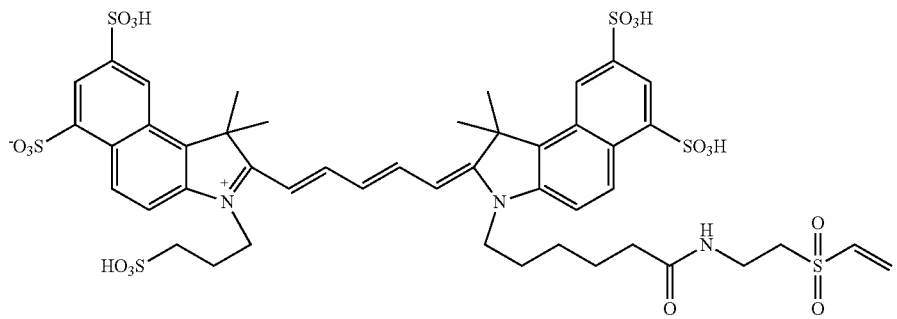

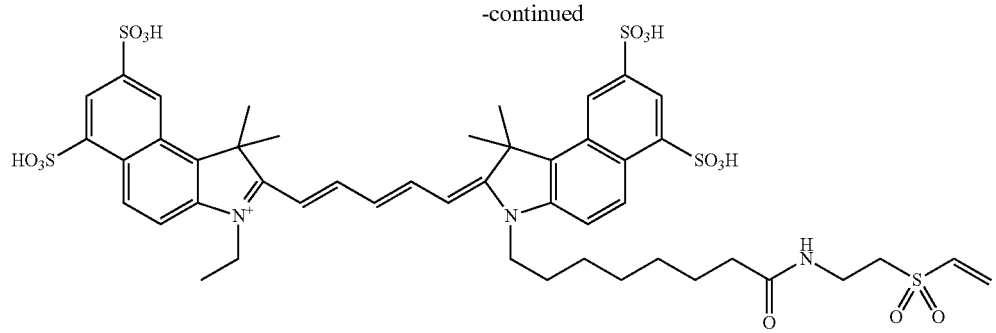

-continued

3. The benzindocyanine compound according to claim 1, wherein the fluorescence wavelength range of the compound represented by Chemical Formula 1 is 500-800 nm.

4. The benzindocyanine compound according to claim 1, wherein the compound represented by Chemical Formula 1 is attached as a label to a biomolecule, a nanoparticle or an organic compound having an amino group, a hydroxyl group or a thiol group.

5. The benzindocyanine compound according to claim 4, wherein the biomolecule is one selected from a group consisting of protein, peptide, carbohydrate, sugar, fat, antibody, proteoglycan, glycoprotein and siRNA.

6. A method for labeling a substance using the compound of Chemical Formula 1, wherein the substance is a biomolecule, a nanoparticle or an organic compound having an amino group, a hydroxyl group or a thiol group, comprising:
reacting the compound of Chemical Formula 1 with the substance, wherein Chemical Formula 1 is:

Chemical Formula 1:

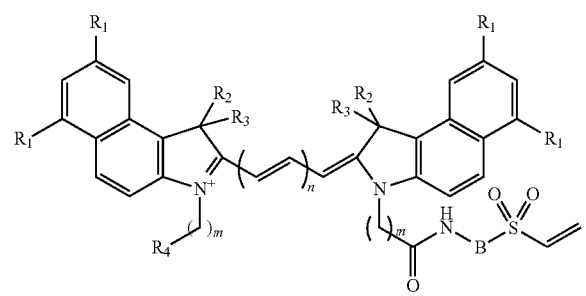

wherein
each of the four $R_1$'s, which are identical or different, is independently hydrogen, a sulfonic acid group or a sulfonate group;
each of the two $R_2$'s, which are identical or different, is independently hydrogen or a $C_1$-$C_6$ alkyl group;
each of the two $R_3$'s, which are identical or different, is independently hydrogen or a $C_1$-$C_6$ alkyl group;
the $R_4$ is hydrogen, a $C_1$-$C_6$ alkyl group, a carboxyl group, a sulfonic acid group, a sulfonate group, —CONH(CH$_2$)$_{L1}$SO$_2$CH=CH$_2$, —CONH-p-(C$_6$H$_4$)SO$_2$CH=CH$_2$ or —CONH-m-(C$_6$H$_4$)SO$_2$CH=CH$_2$, wherein L1 is an integer from 1 to 5;
the B is (CH$_2$)$_{L2}$, p-(C$_6$H$_4$) or m-(C$_6$H$_4$), wherein L2 is an integer from 1 to 5;
the n is an integer from 1 to 5; and
each of the two m's, which are identical or different, is independently an integer from 1 to 10.

7. The method for labeling a substance according to claim 6, wherein the labeling of the substance further comprises binding a vinyl sulfone group of the compound to the amino group, hydroxyl group or thiol group of the biomolecule, nanoparticle or organic compound.

8. The method for labeling a substance according to claim 6, wherein the biomolecule is one selected from a group consisting of protein, peptide, carbohydrate, sugar, fat, antibody, proteoglycan, glycoprotein and siRNA.

9. The method for labeling a substance according to claim 6, wherein reacting comprises reacting the compound of Chemical Formula 1 with the substance in a solvent, wherein the solvent is a buffer selected from the group consisting of phosphate buffer, carbonate buffer and Tris buffer, an organic solvent selected from the group consisting of dimethyl sulfoxide, dimethylformamide and acetonitrile, or water.

10. The method for labeling a substance according to claim 6, wherein reacting comprises reacting the compound of Chemical Formula 1 with the substance in a solvent at pH 5-12.

11. The method for labeling a substance according to claim 6, wherein reacting the compound with the biomolecule, nanoparticle or organic compound at 20-80° C. for 0.5-48 hours.

12. A substance selected from a group consisting of a biomolecule, a nanoparticle and an organic compound, which is labeled with the compound according to claim 1.

13. The substance according to claim 12, wherein the biomolecule is one selected from a group consisting of protein, peptide, carbohydrate, sugar, fat, antibody, proteoglycan, glycoprotein and siRNA.

14. A method for preparing a benzindocyanine compound represented by Chemical Formula 1, comprising:
(a) reacting a compound represented by Chemical Formula 4 with a compound represented by Chemical Formula 5 or 7 to obtain a compound represented by Chemical Formula 6a;

Chemical Formula 4:

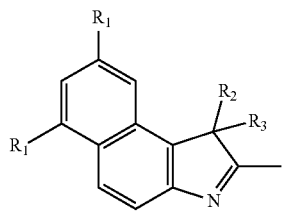

Chemical Formula 5:

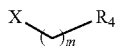

Chemical Formula 6a:

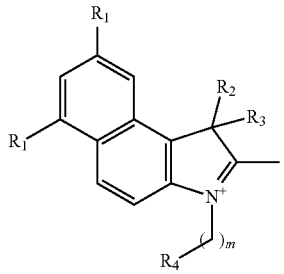

Chemical Formula 7:

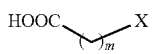

(b) reacting the compound represented by Chemical Formula 6a with a compound represented by Chemical Formula 8 to obtain a compound represented by Chemical Formula 9;

Chemical Formula 8:

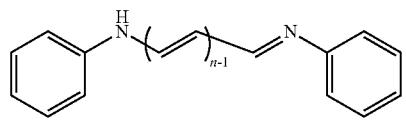

Chemical Formula 9:

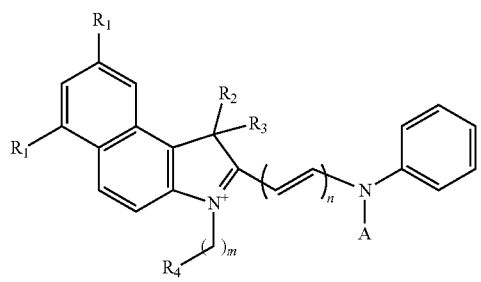

(c) reacting the compound represented by Chemical Formula 9 with a compound represented by Chemical Formula 6b to obtain a compound represented by Chemical Formula 10;

Chemical Formula 6b:

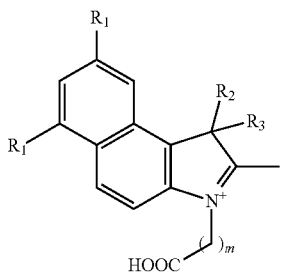

Chemical Formula 10:

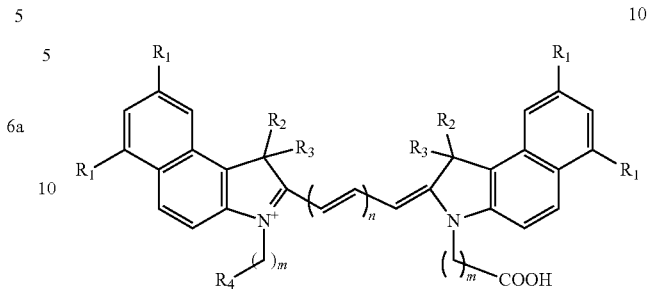

(d) reacting the compound represented by Chemical Formula 10 with 1,1'-carbonyldiimidazole or N,N-disuccinimidyl carbonate to obtain a compound represented by Chemical Formula 11a or 11b; and Chemical Formula 11a:

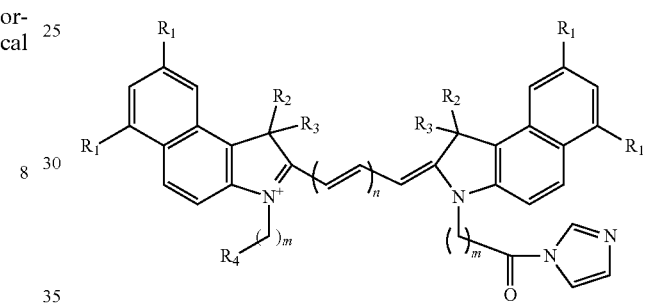

Chemical Formula 11b:

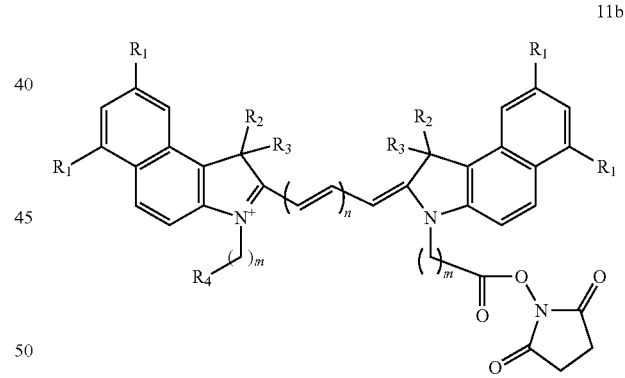

(e) reacting the compound represented by Chemical Formula 11a or 11b with a compound represented by Chemical Formula 12 in the presence of a Hünig's base to obtain a compound represented by Chemical Formula 1:

Chemical Formula 12:

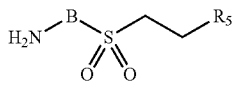

Chemical Formula 1:

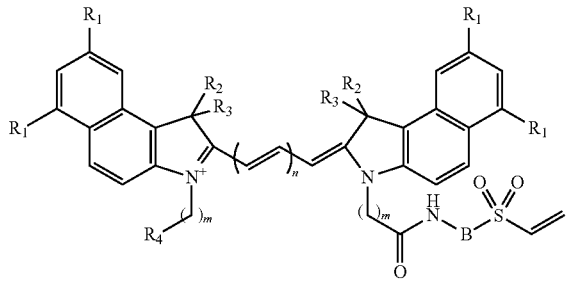

wherein each of the four $R_1$'s, which are identical or different, is independently hydrogen, a sulfonic acid group or a sulfonate group;

each of the two $R_2$'s, which are identical or different, is independently hydrogen or a $C_1$-$C_6$ alkyl group;

each of the two $R_3$'s, which are identical or different, is independently hydrogen or a $C_1$-$C_6$ alkyl group;

the $R_4$ is hydrogen, a $C_1$-$C_6$ alkyl group, a carboxyl group, a sulfonic acid group, a sulfonate group, —CONH(CH$_2$)$_{L1}$SO$_2$CH=CH$_2$, —CONH-p-(C$_6$H$_4$)SO$_2$CH=CH$_2$ or —CONH-m-(C$_6$H$_4$)SO$_2$CH=CH$_2$, wherein L1 is an integer from 1 to 5;

the $R_5$ is a halogen atom selected from a group consisting of fluorine, chlorine, bromine and iodine or a sulfato group (—OSO$_3$H);

the A is hydrogen or an acetyl group;

the X is a halogen atom selected from a group consisting of fluorine, chlorine, bromine and iodine;

the B is (CH$_2$)$_{L2}$, p-(C$_6$H$_4$) or m-(C$_6$H$_4$), wherein L2 is an integer from 1 to 5;

the n is an integer from 1 to 5; and each of the two m's, which are identical or different, is independently an integer from 1 to 10.

* * * * *